(12) United States Patent
Torikai et al.

(10) Patent No.: US 9,873,730 B2
(45) Date of Patent: Jan. 23, 2018

(54) METHOD FOR IMPROVING ANTIBODY

(75) Inventors: Masaharu Torikai, Kikuchi (JP); Toshihiro Nakashima, Kikuchi (JP)

(73) Assignee: THE CHEMO-SERO-THERAPEUTIC RESERACH INSTITUTE, Kumamoto (JP)

( * ) Notice: Subject to any disclaimer, the term of this patent is extended or adjusted under 35 U.S.C. 154(b) by 755 days.

(21) Appl. No.: 11/815,838

(22) PCT Filed: Feb. 7, 2006

(86) PCT No.: PCT/JP2006/302036
§ 371 (c)(1),
(2), (4) Date: Aug. 8, 2007

(87) PCT Pub. No.: WO2006/085518
PCT Pub. Date: Aug. 17, 2006

(65) Prior Publication Data
US 2008/0138860 A1 Jun. 12, 2008

(30) Foreign Application Priority Data

Feb. 8, 2005 (JP) ................................. 2005-032377

(51) Int. Cl.
*C07K 16/00* (2006.01)
*C07K 16/12* (2006.01)
*C07K 16/28* (2006.01)

(52) U.S. Cl.
CPC .......... *C07K 16/00* (2013.01); *C07K 16/1271* (2013.01); *C07K 16/2818* (2013.01); *C07K 2317/21* (2013.01); *C07K 2317/24* (2013.01); *C07K 2317/567* (2013.01); *C07K 2317/94* (2013.01)

(58) Field of Classification Search
USPC ...................................................... 530/387.3
See application file for complete search history.

(56) References Cited

U.S. PATENT DOCUMENTS

| | | | |
|---|---|---|---|
| 5,854,027 A | 12/1998 | Steipe et al. | |
| 6,815,540 B1 * | 11/2004 | Pluckthun et al. | ........ 536/23.53 |
| 6,984,720 B1 * | 1/2006 | Korman et al. | ......... 530/388.22 |

FOREIGN PATENT DOCUMENTS

| | | |
|---|---|---|
| EP | 0957166 A1 | 11/1999 |
| WO | 96/02574 A1 | 2/1996 |
| WO | 98/02462 A1 | 1/1998 |
| WO | 9810070 A1 | 3/1998 |
| WO | 03008451 A2 | 1/2003 |

OTHER PUBLICATIONS

Honegger (Exp. Pharm., 181:47-68, 2008).*
Honegger et al (Pro. Engin., 22(3):121-134, 2009.*
Bentley et al (Cell, 24(3):613-623, 1981 (abstract only)).*
Ewert, et al.,"Stability improvement of antibodies for extracellular and intracellular applications: CDR grafting to stable frameworks and structure-based framework engineering," Methods: A Companion to Methods in Enzymology, 2004, pp. 184-199, vol. 34, No. 2, Academic Press Inc., New York, NY, US.
Saldanha, et al.,"A single backmutation in the human KIV framework of a previously unsuccessfully humanized antibody restores the binding activity and increases the secretion in cos cells," Molecular Immunology, 1999, pp. 709-719, vol. 36, Pergamon, GB.
E. C. Ohage et al., "{beta}-Turn Propensities as paradigms for the analysis of structural motifs to engineer protein stability", Protein Science, (1997) vol. 6, pp. 233-241.
B. Steipe et al., "Sequence Statistics Reliably Predict Stabilizing Mutations in a Protein Domain", J. Mol. Biol. (1994) vol. 240, pp. 188-192.
J. P. L. Cox et al., "A directory of human germ-line V segments reveals a strong bias in their usage", Eur. J. Immunol., (1994), vol. 24, pp. 827-836.
M. Jaeger et al., "The rate-limiting steps for the folding of an antibody scFv fragment", FEBS Letters, (1997), vol. 418, pp. 106-110.
T. Hestercamp et al., "*Escherichia coli* trigger factor is a prolyl isomerase that associates with nascent polypeptide chains", Proc. Natl. Acad. Sci. USA., Apr. 1996, vol. 93, pp. 4437-4441.
H. Lilie et al., "Association of Antibody Chains at Different Stages of Folding: Prolyl Isomerization Occurs after Formation of Quaternary Structure", J. Mol. Biol. (1995) vol. 248, pp. 190-201.
Q. A. Valent et al., "Early events in preprotein recognition in *E.coli*: interaction of SRP and trigger factor with nascent polypeptides", EMBO J. (1995), vol. 14, No. 22, pp. 5494-5505.
W. Zhang et al., "Site-specific mutagenesis of murine anti-human TNF-a Fab gene and its expression in *E.coli*", Bei-Fen, Chin. J. Cell. Mol. Immunol., (2003), vol. 19, No. 4, pp. 338-340.
J. W. Saldanha et al., "A single backmutation in the human kIV framework of a previously unsuccessfully humanized antibody restores the binding activity and increases the secretion in cos cells", Mol. Immunol. (1999) vol. 36, pp. 709-719.
I. Benhar et al., "Identification of Residues that Stabilize the Single-chain Fv of Monoclonal Antibodies B3", J. Biol. Chem. (1995), vol. 270, No. 40, pp. 23373-23380.
N. Hugo et al., "VL position 34 is a key determinant for the engineering of stable antibodies with fast dissociation rates", Protein Engineering, (2003), vol. 16, No. 5, pp. 381-386.
S. Jung et al., "Selection for Improved Protein Stability by Phage Display", J. Mol. Biol., (1999), vol. 294, pp. 163-180.
P. Martineau et al., "Expression of an Antibody Fragment at High Levels in the Bacterial Cytoplasm", J. Mol. Biol. (1998), vol. 280, pp. 117-127.

(Continued)

*Primary Examiner* — Brad Duffy
(74) *Attorney, Agent, or Firm* — Browdy and Neimark, PLLC

(57) ABSTRACT

The present invention provides for a method for improving properties of an antibody such as an expression level and stability. A method for obtaining an antibody with an improved expression level and/or stability by modifying a human antibody or a humanized antibody, characterized by that at least any one of the amino acid residues at position 8, 12, 15 or 18 (according to Kabat numbering) in a light chain variable region (hereinafter referred to as "VL chain") of a human antibody or a humanized antibody is substituted with a different amino acid other than proline or cysteine, and a human antibody or a humanized antibody or a human antibody fragment or a humanized antibody fragment with an improved expression level and/or stability which are obtained by said method.

13 Claims, 12 Drawing Sheets

(56) References Cited

OTHER PUBLICATIONS

G. Vriend et al., "Prediction and analysis of structure, stability and unfolding of thermolysin-like proteases", J. Computer-Aided Mol. Design, (1993), vol. 7, pp. 367-396.

A. Woern et al., "Mutual Stabilization of VL and VH in Single-Chain Antibody Fragments, Investigated with Mutants Engineered for Stability", Biochem. (1998), vol. 37, pp. 13120-13127.

A. Knappik et al., "Engineered turns of a recombinant antibody improve its in vivo folding", Protein Engineering, (1995), vol. 8, No. 1, pp. 81-89.

S. Ewert et al., "Structure-Based Improvement of the Biophysical Properties of Immunoglobulin VH Domains with a Generalizable Approach", Biochem. (2003), vol. 42, pp. 1517-1528.

H. P. Brezinschek et al., "Analysis of the Human VH Gene Repertoire—Differential Effects of Selection and Somatic Hypermutation on Human Peripheral CD5+/IgM+ and CD5-/IgM+ B cells", J. Clin. Invest., (May 1997), vol. 99, No. 10, pp. 2488-2501.

Wörn et al., Stability Engineering of Antibody Single-chain Fv Fragments, J. Mol. Biol., 305:989-1010 (2001).

Office Action in corresponding European Application No. 06 713 179.7-1412, dated Jul. 29, 2014.

Office Action issued in corresponding Japanese Application No. 2011-248541, dated Aug. 6, 2013.

European Search Report issued in corresponding European Application No. EP11179903, dated Nov. 23, 2011.

Nisihara et al., Humanization and epitope mapping of neutralizing anti-human Fas ligand monoclonal antibodies: structural insights into Fas/Fas ligand interaction, Journal of Immunology, 167(6):3266-3275 (2001).

Davies et al., Single Antibody Domains As Small Recognition Units: Design and in Vitro Antigen Selection of Camelized, Human VH Domains With Improved Protein Stability, Protein Engineering, 9(6):531-553 (1996).

Angal et al., A Single Amino Acid Substitution Abolishes the Heterogeneity of Chimeric Mouse/Human (IGG4) Antibody, Molecular Immunology, 30(1):105-108 (1993).

Examination Report dated Aug. 7, 2014 in corresponding European Patent Application No. 11179903.7.

Davies et al., Single Antibody Domains As Small Recognition Units: Design and in Vitro Antigen Selection of Camelized, Human VH Domains With Improved Protein Stability, Protein Engineering, 9(6):531-537 (1996).

Canadian office action for Canadian application Nno. 2596925, dated Dec. 18, 2014.

Kimura S. et al., "Stabilization of *Escherichia coli* Ribonuclease HI by Strategic Replacement of Amino Acid Residues with Those from the the Thermophilic counterpart" The Journal of Biological Chemistry, 267:30:21535-21542 (1992).

Kugler et al "Stabilization and humanization of a single-chain Fv antibody fragment specific for human lymphocute antigen CD19 by designed point mutations and CDR-grafting onto a human framework" Protein Engineering, Design and Selection 22:3:135-147 (2009).

Office Action dated Dec. 10, 2015, in corresponding Canadian Patent Application No. 2596925.

* cited by examiner (a)

pTrc99A-CTLA4-3-1 Fab-E wild (b)

pTrc99A-CTLA4-3-1 Fab-E P15R

METHOD FOR IMPROVING ANTIBODY

TECHNICAL FIELD

The present invention relates to a technique for improving properties of a human antibody such as an expression level and stability through molecular modification of the antibody molecule by amino acid substitution. The technique according to the present invention is expected to be a means for tackling problems such as a lowered level of production, or aggregation, denaturation or inactivation when handling, which have been a great burden to research and development with an antibody.

BACKGROUND ART

An antibody medicament, which is based on the mechanism of biological protection in human, is highly expected since it is a molecular targeting therapeutics which targets a specific functional molecule. Its high efficacy shown in the field of cancer and rheumatism, inter alia, has boosted the world-wide development rush in recent years and its world market scale is thought to keep magnifying for the time being.

Under such social background, marked progress in the technique has been developed in the field of an antibody medicament and antibody engineering. However, some of the obtained clones of antibody molecules have posed much difficulty in their handling due to a low level of expression and/or stability and its solution is not so easy a matter. The problems stated hereinabove have been a great burden to research and development with an antibody.

Another problem confronted in case of an antibody medicament is its cost. Since a comparatively large quantity of antibodies is required for the therapy and also a heavy investment in plant and equipment occurs, increase in not only a burden of patients but also in national expenses for medical treatment will result. Accordingly, an important proposition for the development of an antibody medicament is to improve productivity and to lower its cost.

In the living body, an antibody sequence is produced by a random genetic recombination or mutagenesis occurring while maturation of B cells, among which one having an optimized antibody sequence is selected and proliferated. The optimization chiefly depends upon an antigen-binding capacity. However, a number of factors including stability of domains, interaction between H chain and L chain, interaction between a variable region and a constant region, a protease sensibility and secretion efficiency are thought to complicatedly attribute to the optimization. Thus, natural antibody sequences are not necessarily optimized with respect of stability.

If an isolated antibody clone is expressed as a recombinant protein for analysis, it is sometimes found to be fairly unstable. As a consequence, various problems arise, i.e. (1) an expression level is extremely low; (2) it is expressed not in a soluble form but as inclusion bodies to thereby necessitate refolding; (3) exposure to an acid while purification causes denaturation; or (4) precipitation and denaturation occurs with standing at room temperature or even at 4° C. and thus the reactivity disappeared.

For resolving these problems, the first approach may be investigation of optimal conditions of operations or buffers for respective antibody clones. However, the investigation would not only require much labor and cost but in some cases, by failure of dissolving the problems, might drive a research worker into giving-up of the subsequent analysis or development of an antibody clone which may have had a promising reactivity.

The second approach may be a molecular modification such as amino acid substitution or conversion of a molecular form for aiming at the improvement of the properties of an antibody. In general, modification for improving protein stability includes transplantation of more conserved amino acids from other homologous sequences, and rational design via computer modeling for increasing hydrophilicity on the molecular surface or increasing hydrophobicity within the interior of hydrophobic core to enhance the strength of packing (Non-patent reference 1).

With respect to the improvement of stability or an expression level of an antibody molecule via amino acid substitution, many of previous reports are concerned with characteristic amino acid modification for sequences of respective antibody clones but there are known only few techniques for modification that may be generalized. Such techniques for modification capable of generalization includes amino acid substitution at one or two sites in VH to improve stability of a single chain antibody (scFv) as reported by Worn et al. (Non-patent reference 2); amino acid substitution at one or plural sites in VH to improve an expression level of Fv fragments and to inhibit aggregation reaction as reported by Knappik et al. (Non-patent reference 3); amino acid substitution at one or two sites in VL to improve stability of a VL domain as reported by Steipe et al. (Non-patent reference 4); and amino acid substitution at position 34 (according to Kabat numbering) in VL to improve stability and an expression level of scFv as reported by Hugo et al. (Non-patent reference 5). However, the objective antibodies subject to modification by all these reports are mouse antibodies.

For the use as an antibody medicine, a mouse antibody is recognized as a foreign substance and excluded due to its high antigenicity when administered to human. Thus, it would be difficult to use a mouse antibody as a medicament for therapy of diseases. For dissolving this problem, a mouse monoclonal antibody may be converted to a chimeric antibody using a protein engineering technique. However, a mouse chimeric antibody still contains sequences derived from mice amounting to 30% or more and thus its repetitive or prolonged administration will lead to production of an antibody that inhibits the activity of the chimeric antibody administered to thereby not only extremely lower the efficacy of the medicament but to induce severe adverse side effects.

Therefore, a main approach for solving these problems is to construct a humanized antibody wherein a complementarity determining regions (CDRs) from a mouse variable region are transplanted into a human variable region or a human antibody having sequences completely derived from human.

On the other hand, there is a report by Ewert et al. (Non-patent reference 6) in which amino acid substitution is done for a human antibody at one or plural sites in VH to allow for the improvement of stability and an expression level of scFv. However, the human antibody modified by Ewert et al. is of VH6 family and a frequency in use of the genes belonging to said family is as low as 1.4 to 2.4% (Non-patent reference 7), which renders their technique not being widely feasible one.

As described above, since a specific antibody targeting a disease-related antigen is extremely useful in the clinical field such as human diagnosis and therapy, establishment of the technique for preparing an antibody possessing all the features of high antigen specificity, low immunogenicity and high productivity has earnestly been desired.

Non-patent reference 1: Vriend et al., *J. Comput. Aided Mol. Des.*, 7 (4), p. 367-396 (1993)

Non-patent reference 2: Worn et al., *Biochemistry*, 37, p. 13120-13127 (1998)

Non-patent reference 3: Knappik et al., *Protein Eng.*, 8 (1), p. 81-89 (1995)

Non-patent reference 4: Steipe et al., *J. Mol. Biol.*, 240, p. 188-192 (1994)

Non-patent reference 5: Hugo et al., *Protein Eng.*, 16 (5), p. 381-386 (2003)

Non-patent reference 6: Ewert et al., *Biochemistry*, 42, p. 1517-1528 (2003)

Non-patent reference 7: Brezinschek et al., *J. Clin. Invest.*, 99 (10), p. 2488-2501 (1997)

DISCLOSURE OF THE INVENTION

Technical Problem to be Solved by the Invention

A technical problem to be solved by the present invention is to establish a general method for improving an antibody starting from a human antibody or a humanized antibody, which are known to exhibit low immunogenicity to human, so as to obtain an antibody with high productivity and excellent stability while low immunogenicity and specific binding capacity are maintained.

Means for Solving the Problems

Under the circumstances, the present inventors have earnestly continued research activities and as a result succeeded in significantly improving expression and stability of an antibody by substituting an amino acid or amino acids in a light chain variable region (VL chain) of a human antibody with a different amino acid sequence to thereby complete the present invention. More specifically, the present invention is characterized by that at least any one of the amino acid residues at position 8, 12, 15 or 18 (according to Kabat numbering) in a light chain variable region (hereinafter referred to as "VL chain") of a human antibody is substituted with a different amino acid other than proline or cysteine.

Thus, the present invention encompasses the inventions (1) to (18) as described hereinbelow.

(1) A method for obtaining an antibody with an improved expression level and/or stability by modifying a human antibody or a humanized antibody, characterized by that at least any one of the amino acid residues at position 8, 12, 15 or 18 (according to Kabat numbering) in a light chain variable region (hereinafter referred to as "VL chain") of a human antibody or a humanized antibody is substituted with a different amino acid other than proline or cysteine.

(2) The method according to (1) wherein at least any one of proline at position 8, 12, 15 or 18 or an amino acid residue at position 15 in a VL chain is substituted with a different amino acid other than proline or cysteine.

(3) The method according to (1) or (2) wherein the amino acid residue at the respective position after substitution is selected from any one of the amino acids as described below:
  position 8: Gly, Thr, Arg or Ser
  position 12: Ser, His, Val, Gly, Leu, Arg, Phe, Met or Glu
  position 15: Arg, Ser, Gly or Phe
  position 18: Arg, Ser, Phe, Ala, Trp, Leu or Gln.

(4) The method according to any one of (1) to (3) wherein said VL chain belongs to any one of human Vκ1 family, human Vκ2 family or human Vκ3 family.

(5) The method according to any one of (1) to (4) wherein the amino acid residue at the respective position after substitution in the VL chain belonging to human Vκ1 family is selected from any one of the amino acids as described below:
  position 8: Gly, Thr, Arg or Ser
  position 15: Arg or Ser.

(6) The method according to (5) wherein FR1 of said VL chain belonging to human Vκ1 family prior to substitution has the sequence from DPK9 (GenBank Accession No. X59315; SEQ ID NO:31).

(7) The method according to (5) or (6) wherein FR1 of the VL chain belonging to human Vκ1 family after substitution has the amino acid sequence selected from the amino acid sequences as depicted in SEQ ID NO: 2 to 7.

(8) The method according to any one of (1) to (4) wherein the amino acid residue at the respective position after substitution in the VL chain belonging to human Vκ2 family is selected from any one of the amino acids as described below:
  position 12: Ser, His, Val, Gly, Leu, Arg, Phe, Met or Glu
  position 15: Arg
  position 18: Arg, Ser, Phe, Ala, Trp, Leu or Gln.

(9) The method according to (8) wherein FR1 of said VL chain belonging to human Vκ2 family prior to substitution has the sequence from DPK18 (GenBank Accession No. X63403; SEQ ID NO:32).

(10) The method according to (8) or (9) wherein FR1 of the VL chain belonging to human Vκ2 family after substitution has the amino acid sequence selected from the amino acid sequences as depicted in SEQ ID NO: 9 to 25.

(11) The method according to any one of (1) to (4) wherein the amino acid residue at the respective position after substitution in the VL chain belonging to human Vκ3 family is selected from any one of the amino acids as described below:
  position 15: Arg, Ser, Gly or Phe.

(12) The method according to (11) wherein FR1 of said VL chain belonging to human Vκ3 family prior to substitution has the sequence from DPK22 (GenBank Accession No. X93639; SEQ ID NO:33).

(13) The method according to (11) or (12) wherein FR1 of the VL chain belonging to human Vκ3 family after substitution has the amino acid sequence selected from the amino acid sequences as depicted in SEQ ID NO: 27 to 30.

(14) The method according to any one of (1) to (13) wherein said antibody is an intact antibody, or an antibody fragment such as Fab, Fab', F(ab')$_2$, scAb, scFv, diabody [a recombinant dimer antibody consisting of homologous or heterologous heavy chain variable region (VH chain) and VL chain connected by a short linker peptide] or scFv-Fc; or a fused antibody or a fused antibody fragment with other proteins; or an antibody or an antibody fragment labeled with a low molecular weight compound; or an antibody or an antibody fragment modified with a high molecular weight compound.

(15) The method according to any one of (1) to (14) wherein the amino acid substitution is done by a genetic recombination technique.

(16) A human antibody or a humanized antibody or a human antibody fragment or a humanized antibody fragment with an improved expression level and/or stability which are obtained by the method as set forth in any one of (1) to (14).

(17) A method for preparing an antibody with an improved expression level and/or stability in which at least any one of the amino acid residues at position 8, 12, 15 or 18 (according to Kabat numbering) in a light chain variable region (hereinafter referred to as "VL chain") of a human antibody or a humanized antibody or a human antibody fragment or a humanized antibody fragment is substituted with a different amino acid other than proline or cysteine, which comprises:

preparing a gene coding for an amino acid sequence of said human antibody or said humanized antibody or said human antibody fragment or said humanized antibody fragment, each comprising the amino acid sequence of the VL chain after substitution;

transforming a host of eukaryotic or prokaryotic organisms with said gene;

expressing said human antibody or said humanized antibody or said human antibody fragment or said humanized antibody fragment from said host; and recovering said human antibody or said humanized antibody or said human antibody fragment or said humanized antibody fragment.

(18) A human antibody or a humanized antibody or a human antibody fragment or a humanized antibody fragment with an improved expression level and/or stability which are prepared by the method as set forth in (17).

MORE EFFICACIOUS EFFECTS THAN PRIOR ART

According to the present invention, as a consequence of molecular modification of a human antibody molecule via amino acid substitution, it becomes possible to extremely improve the properties of an antibody such as its expression level and stability. The technique according to the present invention is usable as a means for tackling the problems such as a lowered level of production, or aggregation, denaturation or inactivation when handling, which have been a great burden to research and development with an antibody.

Furthermore, the method for improving an antibody according to the present invention may widely be used for the development of an antibody medicine as a diagnostic or therapeutic agent since it aims at modification of an amino acid residue in a framework region starting from a human antibody or a humanized antibody. Also, since only a single amino acid residue is modified, a concern about antigenic induction when administered to human may be minimized.

Viewing that the improvement of heat stability through molecular modification is reported to increase targeting of tumors in vivo (Willuda et al., *Cancer Res.*, 59, p. 5758-5767 (1999)), it is expected that the improvement of stability leads to the increase in efficacy. As such, the method for improving an antibody according to the present invention is expected to much contribute to the development of an antibody therapy. Furthermore, since an antibody may be applied to not only the medical field but also other various fields, the present invention is expected to be widely applicable to various fields such as related researches or progress of industry.

Accordingly, a human antibody or a humanized antibody or a human antibody fragment or a humanized antibody fragment obtained by the method of the present invention excels in an expression level and/or stability, may decrease damage due to the loss of the activity or the formation of aggregation during a purification step, and may provide utility in antibody production or purification step. Besides, as a matter of course, since the method of the present invention may provide a human antibody molecule or a humanized antibody molecule with excellent stability, it would be able to provide many choices in design of pharmaceutical preparations and thus great advantage for their production.

BEST MODE FOR CARRYING OUT THE INVENTION

Figure 1:
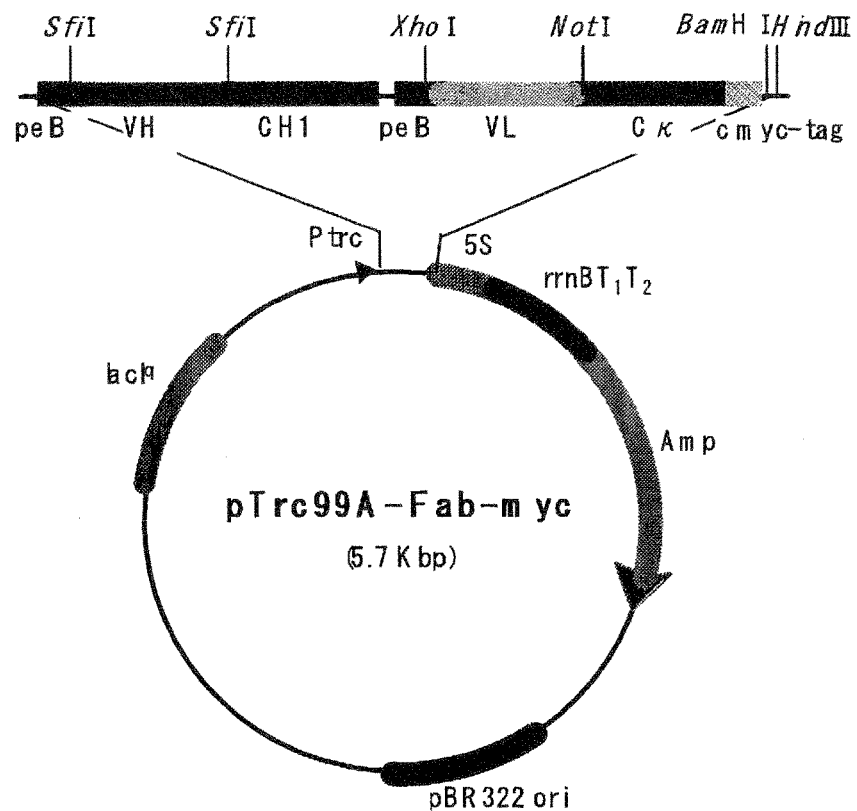
FIG. 1 shows a structure of the plasmid used for expression of Fab.
Figure 2:
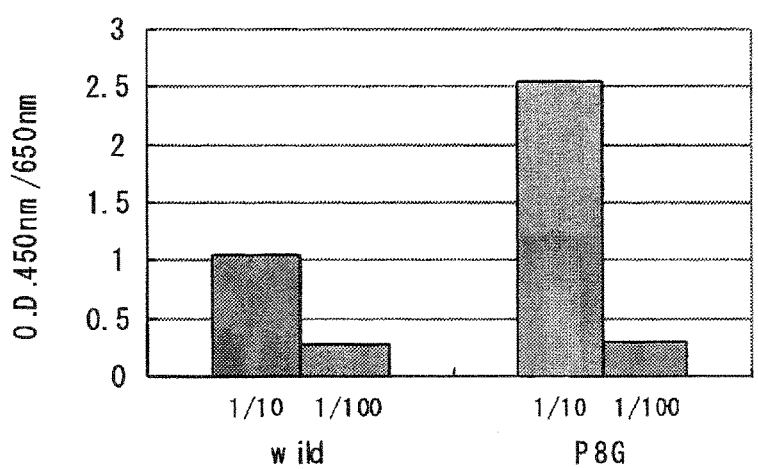
FIG. 2 is a graph showing comparison between a wild-type SEB3-2-7 and its modified antibody at position 8 in L chain for their expression level of a functional Fab protein in periplasm fractions in ELISA.
Figure 3:
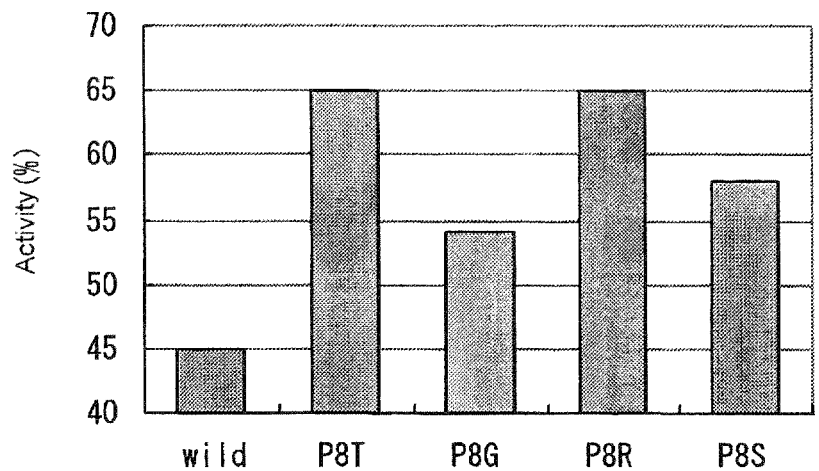
FIG. 3 is a graph showing comparison between a wild-type SEB3-2-7 and its modified antibodies at position 8 in L chain for their heat stability when treated at 42° C. in ELISA.
Figure 4:
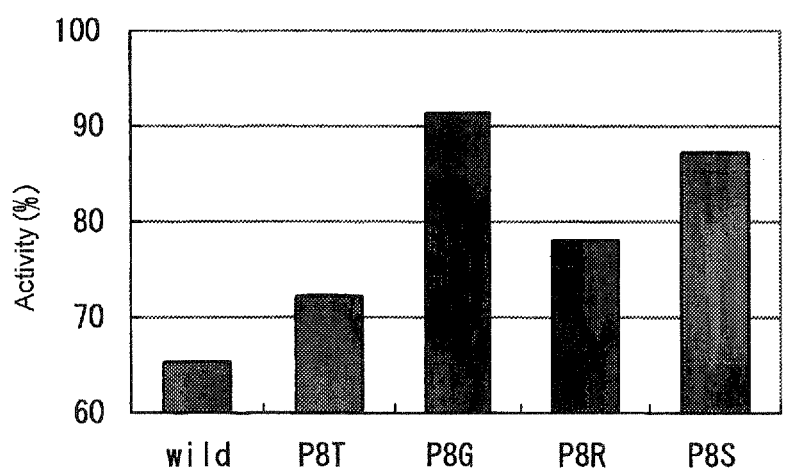
FIG. 4 is a graph showing comparison between a wild-type SEB3-2-7 and its modified antibodies at position 8 in L chain for their tolerance against an acid when treated at pH 4.5 in ELISA.
Figure 5:
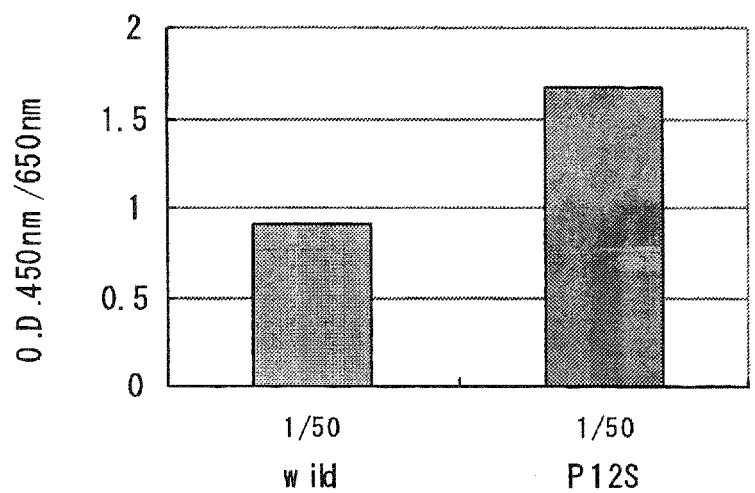
FIG. 5 is a graph showing comparison between a wild-type RNOK203 and its modified antibody at position 12 in L chain for their expression level of a functional Fab protein in culture supernatant in ELISA.
Figure 6:
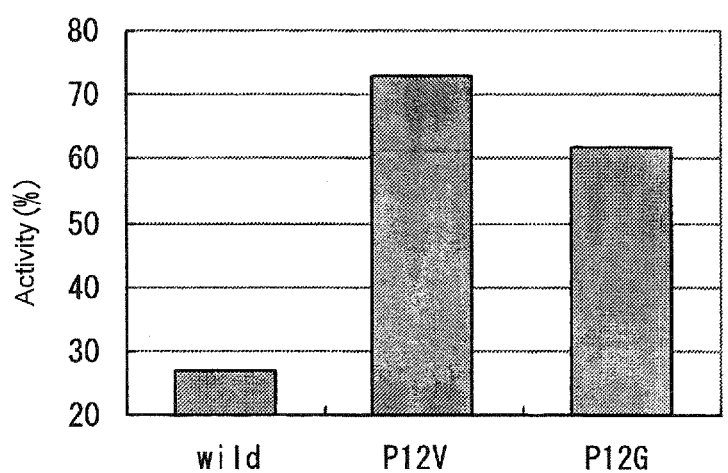
FIG. 6 is a graph showing comparison between a wild-type RNOK203 and its modified antibodies at position 12 in L chain for their heat stability when treated at 40° C. in ELISA.

VL chain of a human antibody to be modified includes λ chain and κ chain, among which κ chain may preferably be used by reasons that 97% of mouse L chain is κ chain ("*Menekigaku Jiten*" (*Dictionary of Immunology*), 2nd Ed., 2001, TOKYO KAGAKU DOJIN CO., LTD.) and thus human Vκ is used as a template sequence in most cases of humanization technique and that κ chain is also major, i.e. 67%, in human L chain (Knappik et al., *J. Mol. Biol.*, 296, p. 57-86 (2000)).

In addition, it is known that human Vκ includes families of Vκ1 to Vκ6. A frequency in use of Vκ1, Vκ2 and Vκ3 in total amounts to 92% to cover most of human Vκ (Foster et al., *J. Clin. Invest.*, 99 (7), p. 1614-1627 (1997)). Thus, any of these three families, Vκ1, Vκ2 and Vκ3, may preferably be used.

As a strategy for antibody modification, amino acid substitution was investigated targeting proline (Pro; P), the amino acid which is in a framework (FR) 1 region important for maintenance of steric structure of VL chain of a humanized antibody and is known to be rate-determining for folding and to destroy α helix and β sheet structures.

Specifically, any one of the amino acid residues at position 8, 12, 15 or 18 in VL chain of a human antibody or a humanized antibody was targeted for modification. As used herein, the identification of the position of amino acid residues in VL chain of an antibody was done in accordance with the numbering scheme by Kabat et al. (Kabat, E. A. et al., *Sequences of Proteins of Immunological Interest*, 5th Ed., NIH Publication No. 91-3242, 1991).

For modification, most of the previous reports were concerned with approach by rational design as described above. As for the technique by transplantation of highly conserved amino acid residues, an antibody sequence as selected in nature is the consequence of choice via complicated attribution of a number of factors such as stability of domains, interaction between H chain and L chain, interaction between a variable region and a constant region, a protease sensibility and secretion efficiency out of cells. Thus, an antibody sequence in nature is not necessarily optimized with respect to stability and hence this technique has limitation. Also, approach using computer modeling will not guarantee actual stability in spite of much labor and thus is not an efficient approach at present.

The present inventors thus investigated by evolutionary engineering technique, i.e. substituted the amino acid residues targeted for modification with any amino acid at random and selected modified antibodies with desired properties from the group obtained.

As a result, as described in Examples hereinbelow, it was verified that the improvement of an expression level and stability could be observed when any one of the following amino acid substitutions was induced in FR1 (1st to 23rd) of VL chain:

position 8: Gly, Thr, Arg or Ser position 12: Ser, His, Val, Gly, Leu, Arg, Phe, Met or Glu position 15: Arg, Ser, Gly or Phe position 18: Arg, Ser, Phe, Ala, Trp, Leu or Gln.

Original sequences (wild) of FR1 of VL chain prior to substitution typically include the following amino acid sequences:

```
Vκ1 (Anti-SEB Ab SEB3-2-7):
DIVMTQSPSSLSASVGDTVTITC        (SEQ ID NO: 1)

Vκ2 (Anti-FasL Ab RNOK203):
DVVMTQTPLSLPVTLGQPASISC        (SEQ ID NO: 8)

Vκ3 (Anti-CTLA-4 Ab CTLA4-3-1):
EIVLTQSPGTLSLSPGERATLSC        (SEQ ID NO: 26)
```

More specifically, modification was performed as described below in accordance with the present invention and the obtained antibodies were assessed for their expression level and stability (i.e. tolerance against heat, tolerance against an acid, tolerance against freeze-thawing, etc.) to prove remarkable improvement in all the obtained antibodies. As used hereinbelow, the symbol "–" means the amino acid residue that is identical to that of a wild-type antibody.

```
(1) Vκ1
Wild:   DIVMTQSPSSLSASVGDTVTITC    (SEQ ID NO: 1)

P8G:    -------G---------------    (SEQ ID NO: 2)

P8T:    -------T---------------    (SEQ ID NO: 3)

P8R:    -------R---------------    (SEQ ID NO: 4)

P8S:    -------S---------------    (SEQ ID NO: 5)
```

-continued

```
V15R:       --------------R--------    (SEQ ID NO:  6)

V15S:       --------------S--------    (SEQ ID NO:  7)

(2) Vκ2
Wild:       DVVMTQTPLSLPVTLGQPASISC    (SEQ ID NO:  8)

P12S:       -----------S-----------    (SEQ ID NO:  9)

P12H:       -----------H-----------    (SEQ ID NO: 10)

P12V:       -----------V-----------    (SEQ ID NO: 11)

P12G:       -----------G-----------    (SEQ ID NO: 12)

P12L:       -----------L-----------    (SEQ ID NO: 13)

P12R:       -----------R-----------    (SEQ ID NO: 14)

P12F:       -----------F-----------    (SEQ ID NO: 15)

P12M:       -----------M-----------    (SEQ ID NO: 16)

P12E:       -----------E-----------    (SEQ ID NO: 17)

L15R:       --------------R--------    (SEQ ID NO: 18)

P18R:       -----------------R-----    (SEQ ID NO: 19)

P18S:       -----------------S-----    (SEQ ID NO: 20)

P18F:       -----------------F-----    (SEQ ID NO: 21)

P18A:       -----------------A-----    (SEQ ID NO: 22)

P18W:       -----------------W-----    (SEQ ID NO: 23)

P18L:       -----------------L-----    (SEQ ID NO: 24)

P18Q:       -----------------Q-----    (SEQ ID NO: 25)

(3) Vκ3
Wild:       EIVLTQSPGTLSLSPGERATLSC    (SEQ ID NO: 26)

P15R:       --------------R--------    (SEQ ID NO: 27)

P15S:       --------------S--------    (SEQ ID NO: 28)

P15G:       --------------G--------    (SEQ ID NO: 29)

P15F:       --------------F--------    (SEQ ID NO: 30)
```

Any of the modifications as specified above have neither been reported nor practiced in prior patents for antibodies derived from animals, let alone for antibodies from human, and thus are firstly investigated in the present application.

In particular, the modified antibody (P15R) with substitution to Arg (R) at position 15 in L chain exhibited drastic effect, namely about 100-fold increase in an expression level of a functional molecule. So much effect with a single amino acid substitution in Fab has never been reported so far. Furthermore, it was demonstrated that the technique for modification for improving an expression level or stability by substituting the 15th amino acid residue in L chain to Arg or Ser may be applicable to at least Vκ1, Vκ2 and Vκ3 families and thus be of wide use.

For the amino acid substitution in accordance with the present invention, modified antibody libraries wherein an arbitrary amino acid was introduced at random at position 8, 12, 15 or 18 in VL chain were constructed using a model antibody. For a model antibody, a human anti-SEB antibody (a clone called "SEB3-2-7"), a human anti-CTLA-4 antibody (a clone called "CTLA4-3-1") and a human anti-human FasL antibody RNOK were used for each of Vκ1, Vκ2 and Vκ3 families, respectively. Using Oligo DNA primers in which a codon of a targeted amino acid in a VL chain gene of the respective antibodies was replaced with a random codon NNK wherein N is A or C or G or T, and K is G or T, a gene of a mutated VL chain was amplified by PCR using a gene of a wild-type VL chain as a template. The thus amplified gene of a mutated VL chain was replaced for the VL region in a wild-type Fab expression plasmid to construct a modified Fab expression plasmid. JM83 was transformed with the obtained plasmid, many clones were obtained and isolated, and expression was induced on 96-well microtiter plate. The expression of Fab in periplasm fractions was assessed by Dot Blot and clones where expression was verified were analyzed for their properties. Fab is an antibody molecule that may be expressed soluble in *E. coli* and convenient for the analysis of properties of a variable region.

By comparison of an expression level of modified Fabs, clones with a higher expression level than that of wild-type Fab were analyzed for their DNA nucleotide sequence to prove that they each contain a single amino acid substitution. The clones were further assessed for their expression level, heat stability, tolerance against an acid and tolerance against freeze-thawing.

An expression level may be assessed and compared between the clones e.g. by inducing expression in shaker-flask culture, and assessing the absorbance of recovered culture supernatant or periplasm fractions by using ELISA as an amount of a functional Fab protein.

Heat stability may be assessed e.g. by diluting and treating with a water-bath at a specified temperature for 2 hours the culture supernatant fractions or the periplasm fractions in which Fab was expressed, restoring the samples at room temperature, performing ELISA, and assessing and comparing between the clones a ratio of the obtained absorbance to that of untreated samples as a residual activity.

Tolerance against an acid may be assessed e.g. by diluting and adjusting to a specified pH for 2 hours the culture supernatant fractions or the periplasm fractions in which Fab was expressed, neutralizing the samples, performing ELISA, and assessing and comparing between the clones a ratio of the obtained absorbance to that of untreated samples as a residual activity.

Tolerance against freeze-thawing may be assessed e.g. by repeating freeze-thawing for specified times for the culture supernatant fractions or the periplasm fractions in which Fab was expressed, performing ELISA, and assessing and comparing between the clones a ratio of the absorbance of the samples subjected to plural freeze-thawing procedures to that of samples subjected to one freeze-thawing procedure as a residual activity.

As a consequence of the assessment of modification, the present inventors have found that the modification as detailed above could improve the properties of an antibody.

In accordance with the present invention, a prepared modified antibody may be utilized not only as an intact antibody but also in the form of an antibody fragment such as Fab, Fab', F(ab')$_2$, scAb, scFv, diabody or scFv-Fc. Such an antibody or an antibody fragment may also be an antibody fused with other proteins or peptides. The expressed antibody may also be labeled with various chemicals or radioactive elements or modified with a synthetic high molecular weight compound such as polyethylene glycol.

An antibody or an antibody fragment modified in accordance with the present invention may be prepared, using a genetic recombination technique and based on sequence information of genes coding for said antibody or antibody fragment, by introducing said genes into a suitable host, e.g.

bacteria, *Bacillus subtilis*, yeast, animal cells, and expressing said antibody or antibody fragment.

As used herein, "a humanized antibody" refers to a human antibody wherein only its complementarity determining regions (CDRs) in a variable region are derived from that of a non-human animal antibody but other variable region than CDR, i.e. a framework region (FR), as well as a constant region are derived from a human antibody.

The present invention is explained in more detail by means of the following Examples but should not be construed to be limited thereto.

Example 1: *E. coli* Strain and DNA (1) *E. coli* Strain

JM83 strain (*Gene,* 33, p. 103-119 (1985)) was used.

(2) Plasmid

Plasmid pTrc99A-Fab-myc codes for each of Fab clones under the control of trc promoter. For allowing for more efficient expression and folding in *E. coli*, the Cys residues at the C-terminal of CH1 and Cκ regions are substituted with Ser to thereby render the molecule lacking disulfide bond between the chains. For easier detection, c-myc tag is added at the C-terminal of L chain. For secretion into periplasm and culture supernatant, pelB sequence signals (Lei et al., *J. Bacteriol.*, 169, p. 4379-4383 (1987)) are inserted upstream both the coding regions of both chains (FIG. 1).

(3) Oligo DNA

Oligo DNAs as used herein were those from SIGMA GENOSYS.

Example 2: Antibody Clones (1) Anti-SEB Antibody SEB3-2-7

This antibody is a human antibody capable of specifically recognizing SEB which was isolated by panning with a recombinant SEB protein from scFv display phage library constructed using as a starting material peripheral blood lymphocytes from 20 healthy volunteers. Its VH has a sequence derived from a segment DP-75 belonging to VH1 family and its VL has a sequence derived from a segment DPK9 (GenBank Accession No. X59315) belonging to Vκ1 family. The amino acid sequence of FR1 of VL domain is shown in SEQ ID NO: 1.

(2) Anti-FasL Antibody RNOK203

This antibody is a humanized antibody which specifically recognizes Fas ligand and has a neutralizing activity as reported by Nakashima et al., *J. Immunol.*, 167, p. 3266-3275 (2001). Its VL has a sequence derived from a segment DPK18 (GenBank Accession No. X63403) belonging to Vκ2 family. The amino acid sequence of FR1 of VL domain is shown in SEQ ID NO: 8.

(3) Anti-CTLA-4 Antibody CTLA4-3-1

This antibody is a human antibody capable of specifically recognizing CTLA-4 which was isolated by panning with a recombinant CTLA-4 protein from scFv display phage library constructed using as starting material peripheral blood lymphocytes from 20 healthy volunteers. Its VH has a sequence derived from a segment DP-25 belonging to VH1 family and its VL has a sequence derived from a segment DPK22 (GenBank Accession No. X59315) belonging to Vκ3 family. The amino acid sequence of FR1 of VL domain is shown in SEQ ID NO: 26.

Example 3: Construction of Wild-Type Fab Expression Plasmid

In contrast to the prior art or the prior reports as described above, most of which used VL domain alone or scFv, modification of an antibody was investigated using Fab in accordance with the present invention. An antibody fragment is advantageous in that it may be expressed in bacteria allowing for quick investigation as compared to IgG which will need expression in an animal cell to thereby necessitate much time and labor for analysis. For a domain alone or scFv, it is known that a change of properties such as lowered antigen affinity, possibly due to structural change, sometimes occurs when sequences of VH and VL are recombined to form IgG molecule but such a change is not likely to occur when Fab is converted to IgG molecule. Accordingly, it is highly possible that the effect of modification observed for Fab molecule may be retained even after the Fab molecule is converted into its corresponding IgG molecule. Viewing that most of the currently available antibody medicines is in the form of IgG molecule, the technique for improving an antibody according to the present invention is expected to much contribute to the field of an antibody medicine.

PCR was performed with Pyrobest DNA Polymerase (TAKARA) for amplification of VH gene and VL gene using scFv plasmid (vector; pCANTAB5E) for SEB3-2-7 and CTLA4-3-1 and IgG expression vector (vector; pCAG: *Gene* 108, p. 193-200, 1991) for RNOK203 as starting material. The VH gene region digested with SfiI and the VL gene region digested with XhoI and NotI were inserted into pTrc99A-Fab-myc vector in order.

Example 4: Transformation

Transformation was performed by electroporation using Gene Pulser (BIO-RAD). JM83 strain was made competent, transformed, applied to LB agar medium containing 50 μg/mL ampicillin, and cultured at 30° C. overnight. The obtained clones were isolated and cultured. The plasmids were prepared by the conventional manner and the DNA sequences were analyzed.

Example 5: DNA Sequencing

A DNA sequence of the modified VL gene was determined using CEQ DTCS Quick Start Kit (BECKMAN COULTER) For the expression strain as constructed, the DNA sequencing proved that it contained the sequence as designed.

Example 6: Construction of Modified Fab Expression Plasmids

Using a wild-type Fab expression plasmid as a template, PCR was performed as described above for amplification of VL gene using Oligo DNAs in which codon at the site for mutation was NNK wherein N is A or C or C or T, and K is G or T. The amplified VL gene was replaced for the VL region of a wild-type Fab expression plasmid. JM83 was transformed with the resulting plasmids and expression was induced for the obtained clones on 96-well microtiter plate.

Example 7: Induction of Fab Expression by Plating Culture

The clones obtained above and a wild-type Fab-expressing strain as a control were inoculated to 2×YT culture containing 50 μg/mL ampicillin on 96-well plate (COSTAR) and cultured at 30° C. for 5 to 6 hours. IPTG was added to the plate at a final concentration of 1 mM and culture was continued overnight to induce Fab expression. After completion of culture, the cells were centrifuged and recovered, suspended in PBS containing 1 mM EDTA and left to stand on ice for 30 minutes. The cells were then centrifuged at 2,000 rpm for 15 minutes and the supernatant was recovered to obtain a periplasm fraction.

Example 8: Dot Blot

Expression level was analyzed by Dot Blot. The periplasm fraction obtained above was spotted on 0.45.mu.m nitrocellulose filter (Millipore) and, following blocking with PBS-0.05% TWEEN20 containing 2% skim milk, Fab expression was detected with peroxidase (HRP)-labeled anti-Fab Ab (CAPPEL). For those clones which were thought to exhibit a higher expression level, the DNA sequences were analyzed as described above and the clones which could prove to undergo single amino acid substitution were assessed as described hereinbelow.

Example 9: Induction of Fab Expression by Shaking Culture

The suspension of *E. coli* cells was applied to LB agar containing 50 μg/mL ampicillin and cultured at 30° C. overnight. The obtained single colony was then inoculated to 2×YT culture containing 50 μg/mL ampicillin and cultured at 30° C. until O.D. at 600 nm becomes 0.5 to 1.0. IPTG was added at a final concentration of 1 mM and culture was continued overnight to induce Fab expression. After completion of culture, the cells were centrifuged and the supernatant was recovered to obtain a supernatant fraction. The precipitated cells were suspended in PBS containing 1 mM EDTA and left to stand on ice for 30 minutes. The cells were then centrifuged at 8,900×g for 15 minutes and the supernatant was recovered as a periplasm fraction.

Example 10: Assessment of Reactivity with SEB by ELISA

The expressed and purified recombinant SEB at 200 ng/100 μL/well was immobilized on an ELISA plate (Nunc) at 4° C. overnight and, after washing, blocked with 1% BSA-PBS at 4° C. overnight. The periplasm fractions or the culture supernatant fractions of wild-type SEB3-2-7/its modified antibody were diluted to 100 μL/well with 1% BSA-PBS and reacted at 37° C. for 1 hour. Detection was performed with a combination of biotin-labeled anti-Kappa Ab (Southern Biotechnology) and peroxidase (HRP)-labeled streptavidin (Vector Lab.). Absorbance at 650 nm/450 nm was measured with Microplate Reader Vmax (Molecular Devices).

Example 11: Assessment of Expression Level of Modified Antibodies at Position 8 in L Chain with SEB3-2-7

The periplasm fractions of a wild-type SEB3-2-7/its modified antibodies were diluted step-wise and compared for their expression level of a functional Fab protein in ELISA. As a result, it was found that P8G modified antibody exhibited an increased expression level (FIG. 2).

Example 12: Assessment of Heat Stability of Modified Antibodies at Position 8 in L Chain with SEB3-2-7

The culture supernatant fractions of wild-type SEB3-2-7/its modified antibodies were diluted to 50 μL/tube with 1% BSA-PBS and treated in a water-bath at 42° C. for 2 hours. The samples were then restored at room temperature and subjected to ELISA where a ratio of the obtained absorbance to that of untreated samples was shown as a residual activity in a graph. As a result, it was found that P8T, P8G, P8R and P8S modified SEB3-2-7 antibodies exhibited increased heat stability (FIG. 3).

Example 13: Assessment of Tolerance Against Acid of Modified Antibodies at Position 8 in L Chain with SEB3-2-7

The culture supernatant fractions of wild-type SEB3-2-7/its modified antibodies were diluted to 50 μL/tube with 1% BSA-PBS and adjusted to pH 4.5 with 1N HCl and a pH meter (HORIBA) and treated at 25° C. for 2 hours. The samples were then adjusted to pH 7 with 1M Tris-HCl (pH 9.5) and subjected to ELISA where a ratio of the obtained absorbance to that of untreated samples was shown as a residual activity in a graph. As a result, it was found that P8T, P8G, P8R and P8S modified SEB3-2-7 antibodies exhibited increased tolerance against an acid (FIG. 4).

Example 14: Assessment of Reactivity with FasL by ELISA

For FasL, a commercially available recombinant Fas Ligand (R&D systems) with His-tag at 50 ng/100 μL/well was immobilized on an NI chelate plate (Nunc) at room temperature for 2 hours. The culture supernatant fractions of wild-type RNOK203/its modified antibody were diluted to 100 μL/well with Block Ace (Dainippon Pharma Co., Ltd.) and reacted at 37° C. for 1 hour. Detection was performed with a combination of biotin-labeled anti-Kappa Ab (Southern Biotechnology) and peroxidase (HRP)-labeled streptavidin (Vector Lab.). Absorbance at 650 nm/450 nm was measured with Microplate Reader Vmax (Molecular Devices).

Example 15: Assessment of Expression Level of Modified Antibodies at Position 12 in L Chain with RNOK203

The culture supernatant fractions of a wild-type RNOK203/its modified antibodies were diluted step-wise and compared for their expression level of a functional Fab protein in ELISA. As a result, it was found that P12S modified antibody exhibited an increased expression level (FIG. 5).

Example 16: Assessment of Heat Stability of Modified Antibodies at Position 12 in L Chain with RNOK203

The culture supernatant fractions of wild-type RNOK203/its modified antibodies were diluted to 50 μL/tube with Block Ace and treated in a water-bath at 40° C. for 2 hours. The samples were then restored at room temperature and subjected to ELISA where a ratio of the obtained absorbance to that of untreated samples was shown as a residual activity in a graph for comparison between the modified antibodies. As a result, it was found that P12S, P12H, P12V, P12G, P12L, P12R, P12F, P12M and P12E modified RNOK203 antibodies exhibited increased heat stability (FIG. 6). Typical results are shown in a graph (FIG. 6) whereas the results of the remaining modified antibodies are summarized in Table 1 for a ratio of the respective residual activity to that of the wild-type antibody.

TABLE 1

| Modified antibodies | Comparison with wild-type (%) |
|---|---|
| P12S | 140 |
| P12H | 150 |
| P12V | 270 |
| P12G | 230 |
| P12L | 250 |
| P12R | 190 |
| P12F | 170 |
| P12M | 140 |
| P12E | 210 |

Example 17: Assessment of Tolerance Against Acid of Modified Antibodies at Position 12 in L Chain with RNOK203

Figure 7:
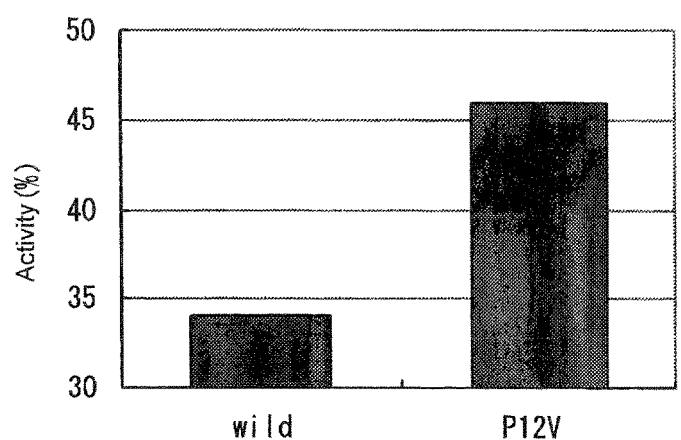
FIG. 7 is a graph showing comparison between a wild-type RNOK203 and its modified antibody at position 12 in L chain for their tolerance against an acid when treated at pH 4.0 in ELISA.

The culture supernatant fractions of wild-type RNOK203/its modified antibodies were diluted to 50 µL/tube with Block Ace and adjusted to pH 4.0 with 1N HCl and a pH meter (HORIBA) and treated at 25° C. for 2 hours. The samples were then adjusted to pH 7 with 1M Tris-HCl (pH 9.5) and subjected to ELISA where a ratio of the obtained absorbance to that of untreated samples was shown as a residual activity in a graph. As a result, it was found that P12V modified RNOK203 antibody exhibited increased tolerance against an acid (FIG. 7).

Example 18: Assessment of Tolerance Against Freeze-Thawing of Modified Antibodies at Position 12 in L Chain with RNOK203

Figure 8:
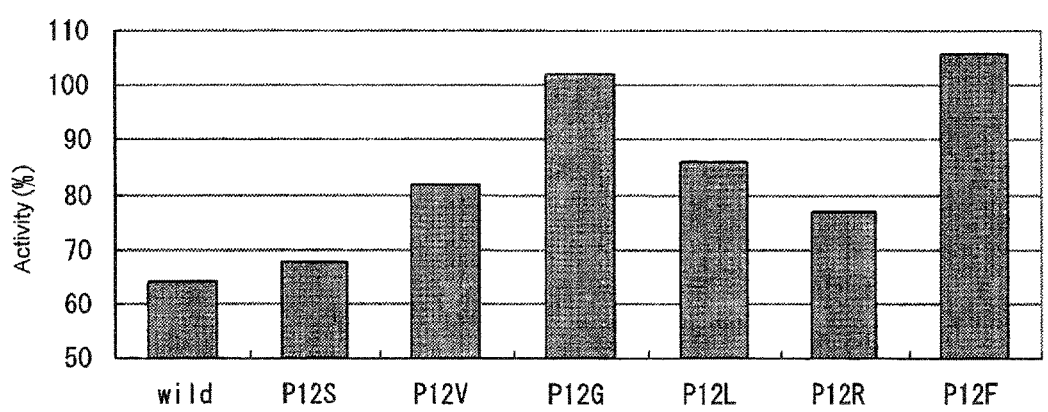
FIG. 8 is a graph showing comparison between a wild-type RNOK203 and its modified antibodies at position 12 in L chain for their tolerance against freeze-thawing in ELISA.

The culture supernatant fractions of wild-type RNOK203/its modified antibodies were subjected to freeze-thawing repeated for either six times or only once and then to ELISA where a ratio of the absorbance obtained from the samples subjected to six freeze-thawing procedures to that of samples subjected to only one freeze-thawing procedure as a residual activity. As a result, it was found that P12S, P12V, P12G, P12L, P12R and P12 modified RNOK203 antibodies exhibited increased tolerance against freeze-thawing (FIG. 8).

Example 19: Assessment of Reactivity with CTLA-4 by ELISA

For CTLA-4, a commercially available recombinant CTLA-4 (R&D systems) at 100 ng/100 µL/well was immobilized on an ELISA plate (Nunc) at room temperature for 1 hour. After washing, the plate was blocked with Block Ace at room temperature for 1 hour. The periplasm fractions of wild-type CTLA4-3-1/its modified antibody were diluted to 100 µL/well with Block Ace and reacted at 37° C. for 1 hour. Detection was performed with a combination of biotin-labeled anti-Kappa Ab (Southern Biotechnology) and per-oxidase (HRP)-labeled streptavidin (Vector Lab.). Absorbance at 650 nm/450 nm was measured with Microplate Reader Vmax (Molecular Devices).

Example 20: Assessment of Expression Level of Modified Antibodies at Position 15 in L Chain with CTLA-4

Figure 9:
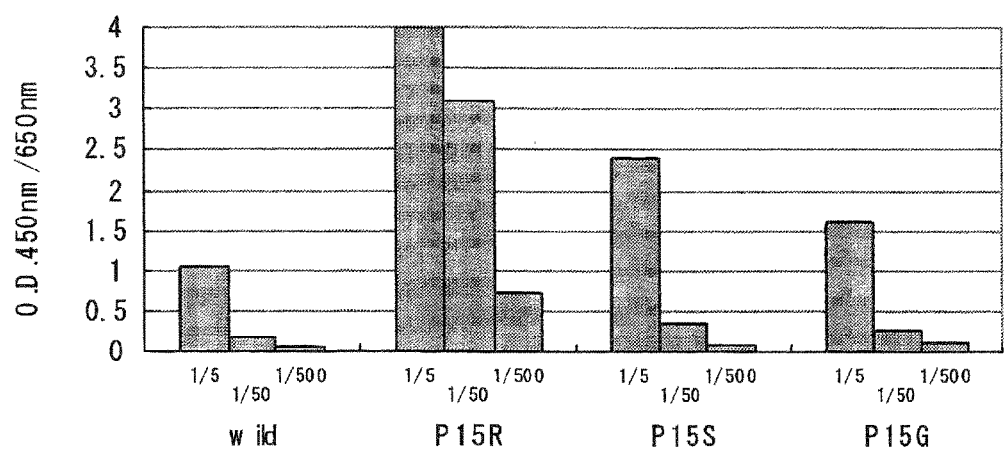
FIG. 9 is a graph showing comparison between a wild-type CTLA4-3-1 and its modified antibody at position 15 in L chain for their expression level of a functional Fab protein in periplasm fractions in ELISA.

The periplasm fractions of a wild-type CTLA4-3-1/its modified antibodies were diluted step-wise and compared for their expression level of a functional Fab protein in ELISA. As a result, it was found that P15R, P15S and P15G modified antibodies exhibited an increased expression level (FIG. 9). In particular, the P15R modified antibody exhibited a drastic effect of as high as about 100-fold increase in an expression level. So much increase in an expression level of a functional Fab protein with merely a single amino acid substitution has never been reported so far.

Figure 10:
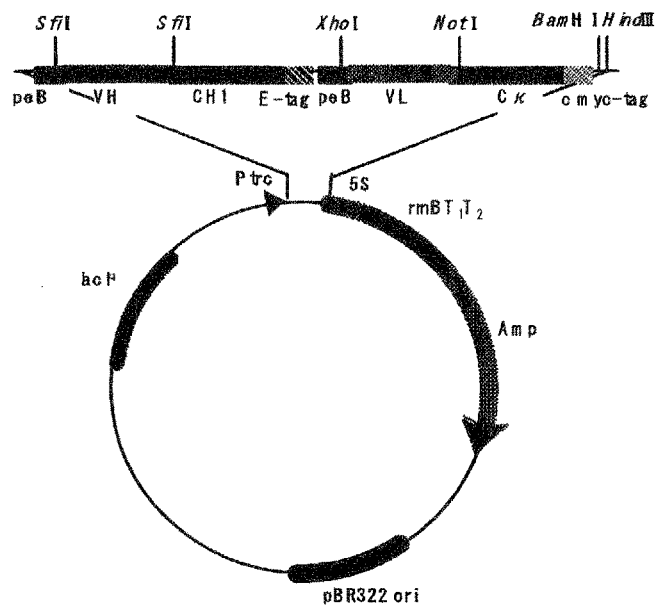
FIG. 10 shows a structure of the expression plasmids for wild-type CTLA4-3-1 Fab, in which a synthetic Oligo DNA coding for E tag is inserted at the C-terminal of Fd chain, and its P15R modified antibody. Panels (a) and (b) show wild-type CTLA4-3-1 Fab and its P15R modified antibody, respectively.
Figure 10:
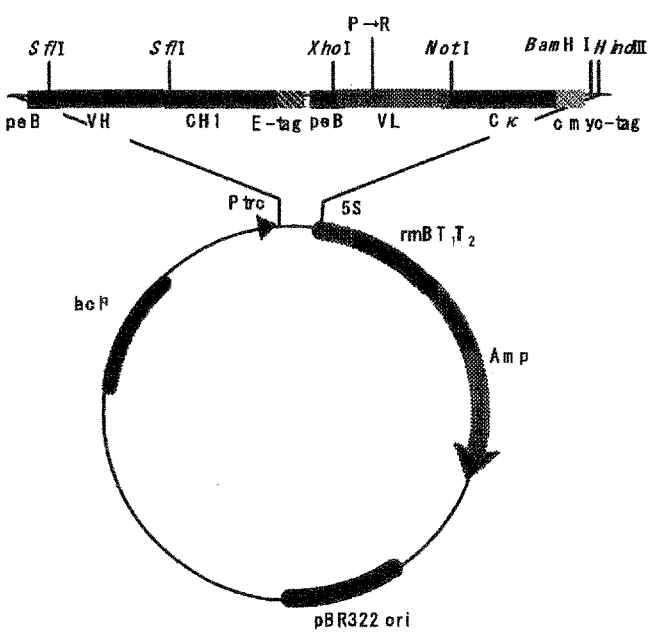

Example 21: Construction of Wild-Type CTLA4-3-1 Fab-E/its P15R Modified Antibodies Expression Plasmid In order to further verify the increased expression level of the P15R modified antibody as observed in Example 20, the Fab expression plasmid was modified. Expression plasmids for wild-type CTLA4-3-1 Fab/its P15R modified Fab were constructed (FIG. 10) wherein a synthetic Oligo DNA coding for E tag was inserted at the C-terminal of Fd chain (i.e. a region of H chain including VH to CH1). Hereinafter, Fab containing Fd chain with E tag is referred to as "Fab-E". JM83 strain as competent cells was transformed with the resulting plasmids and the DNA sequencing proved that they contained the sequences as designed. Thus, it has now become possible to detect Fd chain and L chain both constituting Fab either by the use of E tag for Ed chain or c-myc tag for L chain.

The thus constructed wild-type CTLA4-3-1 Fab-E/its P15R modified Fab-E were subjected to induction of expression by shaking culture as in Example 9 and culture supernatant fractions and periplasm fractions were recovered.

Figure 11:
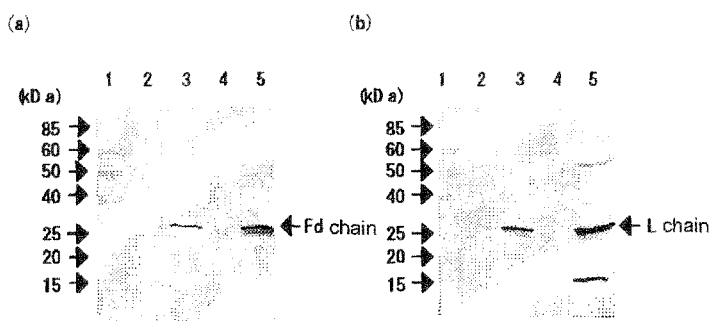
FIG. 11 is a graph showing comparison between a wild-type CTLA4-3-1 Fab-E and its P15R modified antibody for their expression level of Fd chain and L chain in culture supernatant fractions and periplasm fractions in Western blotting. Panel (a) shows the results for Fd chain which was detected with HRP-labeled anti-E tag Ab. Panel (b) shows the results for L chain which was detected with HRP-labeled anti-c-myc tag Ab. Lane 1: marker; Lane 2: wild-type CTLA4-3-1 Fab-E in culture supernatant fractions; Lane 3: P15R modified CTLA4-3-1 Fab-E in culture supernatant fractions; Lane 4: wild-type CTLA4-3-1 Fab-E in periplasm fractions; and Lane 5: P15R modified CTLA4-3-1 Fab-E in periplasm fractions.

Example 22: Assessment of Expression Level of Wild-Type CTLA4-3-1 Fab-E/its P15R Modified Fab-E by Western Blotting The culture supernatant fractions and the periplasm fractions obtained in Example 21 were analyzed by Western blotting to detect Fd chain and L chain. Detection of Fd chain and L chain was performed with HRP-labeled anti-E tag Ab (Amersham Biosciences) and HRP-labeled anti-c-myc tag Ab (Roche), respectively. As a result, neither Fd chain nor L chain could be detected for the wild-type Fab-E whereas bands could be detected for the P15R modified Fab-E at about 27 kDa and about 26 kDa for Fd chain and L chain, respectively, which virtually corresponded to the molecular weights as designed (FIG. 11). These results confirmed that the P15R modification increased expression level of both Fd chain and L chain.

Example 23: Assessment of Expression Level of Wild-Type CTLA4-3-1 Fab-E/its P15R Modified Fab-E by Sandwich ELISA In order to investigate whether Fd chain and L chain are assembled together to form a correct molecular form of Fab, the following sandwich ELISA system was utilized. Anti-c-myc tag Ab 9E10 at 200 ng/100 µL/well was immobilized on an ELISA plate (Nunc) at room temperature for 1 hour. After washing, the plate was blocked with 1% BSA-PBS at room temperature for 1 hour. Each of the fractions were diluted to 100 µL/well with 1% BSA-PBS and reacted at 37° C. for 1 hour. Detection was performed with HRP-labeled anti-E tag Ab. Absorbance at 650 nm/450 nm was measured with Microplate Reader Vmax (Molecular Devices).

Figure 12:
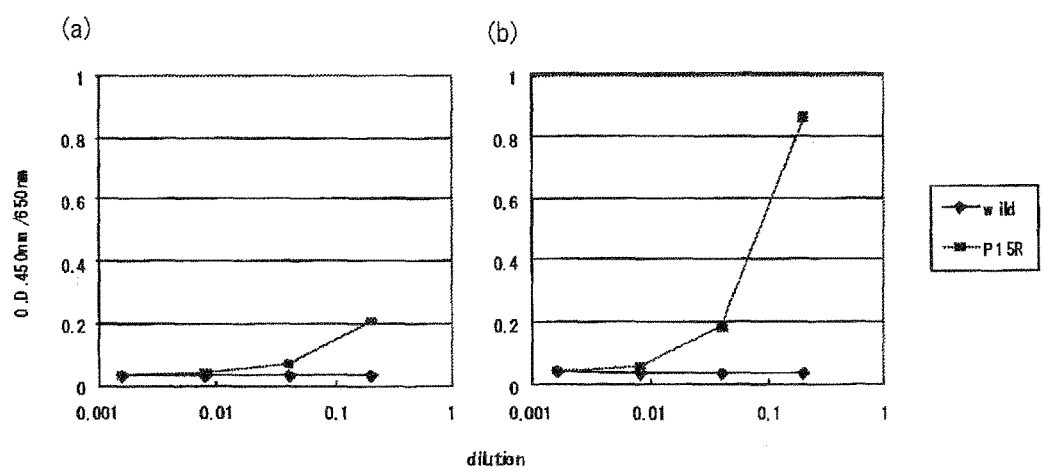
FIG. 12 is a graph showing comparison between a wild-type CTLA4-3-1 Fab-E and its P15R modified antibody for their expression level of Fd chain/L chain complex in culture supernatant fractions and periplasm fractions in sandwich ELISA. Panels (a) and (b) show the results for culture supernatant fractions and periplasm fractions, respectively.

As a result, it was found that, while no detection was observed for wild-type CTLA4-3-1 Fab-E, a concentrationdependent reaction was observed for P15R modified Fab-E with several ten times higher reaction for the periplasm fractions thereof (FIG. 12). These results confirmed that the P15R modification also highly increased an expression level of a complex of Fd chain and L chain.

Example 24: Assessment of Heat Stability of Modified Antibodies at Position 15 in L Chain with CTLA4-3-1

Figure 13:
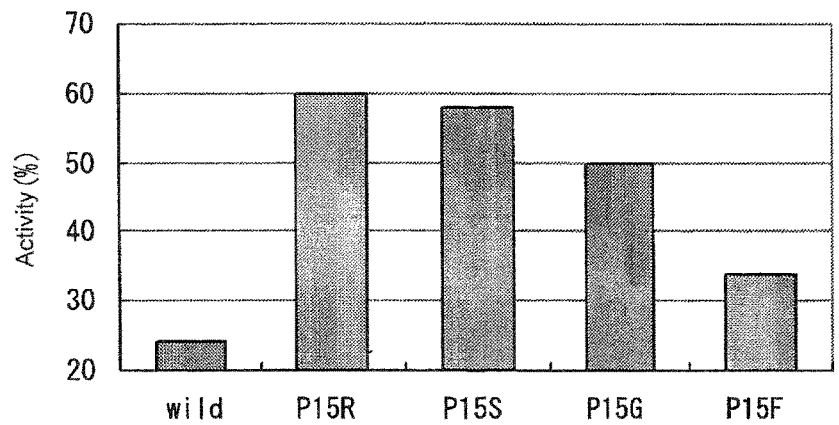
FIG. 13 is a graph showing comparison between a wild-type CTLA4-3-1 and its modified antibodies at position 15 in L chain for their heat stability when treated at 28° C. in ELISA.

The periplasm fractions of wild-type CTLA4-3-1/its modified antibodies were diluted to 50 µL/tube with Block Ace and treated in a water-bath at 28° C. for 2 hours. The samples were then restored at room temperature and subjected to ELISA where a ratio of the obtained absorbance to that of untreated samples was shown as a residual activity in a graph. As a result, it was found that P15R, P15S, P15G and P15F modified CTLA4-3-1 antibodies exhibited increased heat stability (FIG. 13).

Example 25: Assessment of Tolerance Against Acid of Modified Antibodies at Position 15 in L Chain with CTLA4-3-1

Figure 14:
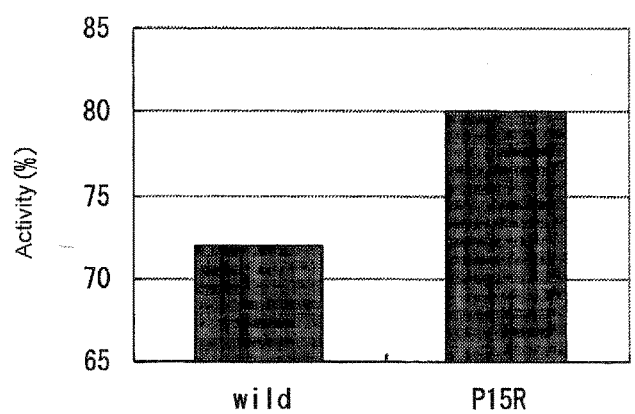
FIG. 14 is a graph showing comparison between a wild-type CTLA4-3-1 and its modified antibodies at position 15 in L chain for their tolerance against an acid in ELISA. Panels (a) and (b) show the results when treated at pH 4.0 and at pH 3.5, respectively.
Figure 14:
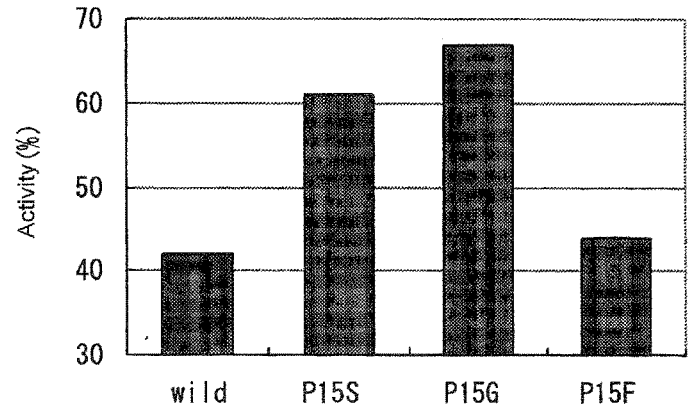

The periplasm fractions of wild-type CTLA4-3-1/its modified antibodies were diluted to 50 µL/tube with Block Ace and adjusted to pH 4.0 or pH 3.5 with 1N HCl and a pH meter (HORIBA) and treated on ice for 2 hours. The samples were then adjusted to pH 7 with 1M Tris-HCl (pH 9.5) and subjected to ELISA where a ratio of the obtained absorbance to that of untreated samples was shown as a residual activity in a graph. As a result, it was found that P15R, P15S, P15G and P15F modified CTLA4-3-1 antibodies exhibited increased tolerance against an acid (FIG. 14).

Example 26: Construction of Modified Antibodies at Position 15 in L Chain of RNOK203

It was investigated whether the same effects observed in Examples 20 to 25 for the modification to Arg or Ser at position 15 in L chain could also be detected for RNOK203 wherein the 15th amino acid residue is Leu.

Using a wild-type Fab expression plasmid as a template, PCR was performed as described above for amplification of VL gene using Oligo DNAs in which codon at position 15 in L chain was CGT(Arg) and TCT(Ser). The amplified VL gene was replaced for the VL region of wild-type Fab expression plasmid. JM83 was transformed with the resulting plasmid and the DNA sequence was analyzed for the obtained clones to prove that they contained the sequences as designed.

Example 27: Assessment of Expression Level of Modified Antibodies at Position 15 in L Chain with RNOK203

Figure 15:
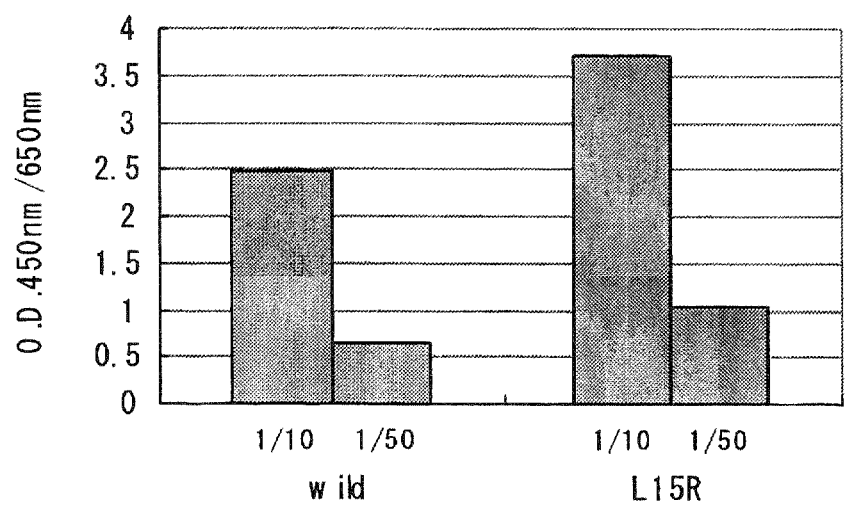
FIG. 15 is a graph showing comparison between a wild-type RNOK203 and its modified antibody at position 15 in L chain for their expression level of a functional Fab protein in culture supernatant fractions in ELISA.

The culture supernatant fractions of a wild-type RNOK203/its modified antibodies were diluted step-wise and compared for their expression level of a functional Fab protein in ELISA. As a result, it was found that L15R modified RNOK203 antibody exhibited an increased expression level (FIG. 15).

Example 28: Assessment of Tolerance Against Acid of Modified Antibodies at Position 15 in L Chain with RNOK203

Figure 16:
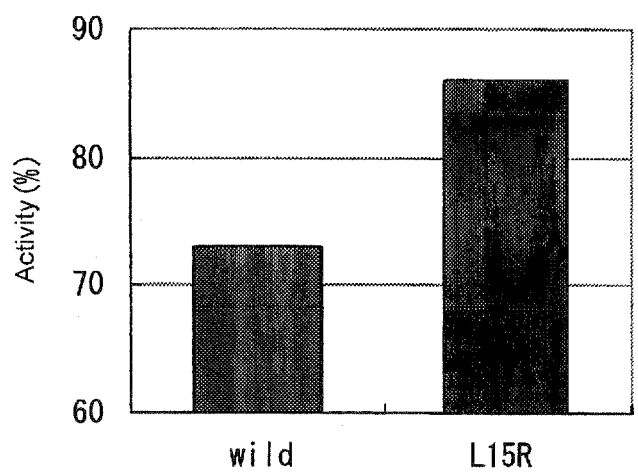
FIG. 16 is a graph showing comparison between a wild-type RNOK203 and its modified antibody at position 15 in L chain for their tolerance against an acid when treated at pH 5.0 in ELISA.

The culture supernatant fractions of wild-type RNOK203/its modified antibodies were diluted to 50 µL/tube with Block Ace and adjusted to pH 5.0 with 1N HCl and a pH meter (HORIBA) and treated at 25° C. for 2 hours. The samples were then adjusted to pH 7 with 1M Tris-HCl (pH 9.5) and subjected to ELISA where a ratio of the obtained absorbance to that of untreated samples was shown as a residual activity in a graph. As a result, it was found that L15R modified RNOK203 antibody exhibited increased tolerance against an acid (FIG. 16).

Example 29: Construction of Modified Antibodies at Position 15 in L Chain of SEB3-2-7

It was investigated whether the same effects observed in Examples 20 to 28 for the modification to Arg or Ser at position 15 in L chain could also be detected for SEB3-2-7 wherein the 15th amino acid residue is Val.

Using a wild-type Fab expression plasmid as a template, PCR was performed as described above for amplification of VL gene using Oligo DNAs in which codon at position 15 in L chain was CGT(Arg) and TCT(Ser). The amplified VL gene was replaced for the VL region of a wild-type Fab expression plasmid. JM83 was transformed with the resulting plasmid and the DNA sequence was analyzed for the obtained clones to prove that they contained the sequences as designed.

Example 30: Assessment of Heat Stability of Modified Antibodies at Position 15 in L Chain with SEB3-2-7

Figure 17:
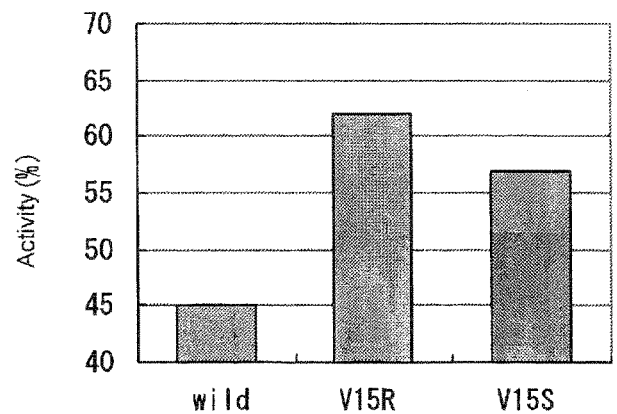
FIG. 17 is a graph showing comparison between a wild-type SEB3-2-7 and its modified antibodies at position 15 in L chain for their heat stability when treated at 42° C. in ELISA.

The culture supernatant fractions of wild-type SEB3-2-7/its modified antibodies were diluted to 50 µL/tube with 1% BSA-PBS and treated in a water-bath at 42° C. for 2 hours. The samples were then restored at room temperature and subjected to ELISA where a ratio of the obtained absorbance to that of untreated samples was shown as a residual activity in a graph. As a result, it was found that V15R and V15S modified SEB3-2-7 antibodies exhibited increased heat stability (FIG. 17).

Example 31: Assessment of Tolerance Against Acid of Modified Antibodies at Position 15 in L Chain with SEB3-2-7

Figure 18:
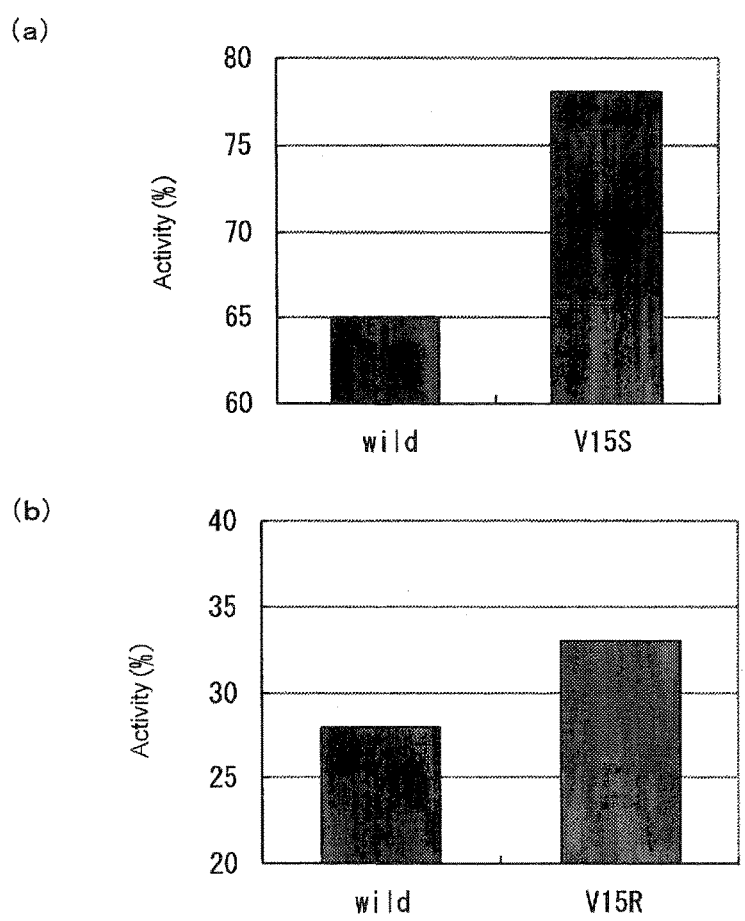
FIG. 18 is a graph showing comparison between a wild-type SEB3-2-7 and its modified antibodies at position 15 in L chain for their tolerance against an acid in ELISA. Panels (a) and (b) show the results when treated at pH 4.5 and at pH 4.0, respectively.

The culture supernatant fractions of wild-type SEB3-2-7/its modified antibodies were diluted to 50 µL/tube with 1% BSA-PES and adjusted to pH 4.5 or pH 4.0 with 1N HCl and a pH meter (HORIBA) and treated at 25° C. for 2 hours. The samples were then adjusted to pH 7 with 1M Tris-HCl (pH 9.5) and subjected to ELISA where a ratio of the obtained absorbance to that of untreated samples was shown as a residual activity in a graph. As a result, it was found that V15R and V15S modified SEB3-2-7 antibodies exhibited increased tolerance against an acid (FIG. 18).

Example 32: Assessment of Heat Stability of Modified Antibodies at Position 18 in L Chain with RNOK203

The culture supernatant fractions of wild-type RNOK203/its modified antibodies were diluted to 50 µL/tube with Block Ace and treated in a water-bath at 45° C. for 2 hours. The samples were then restored at room temperature and subjected to ELISA where a ratio of the obtained absorbance to that of untreated samples was shown as a residual activity in a graph for comparison between the modified antibodies.

Figure 19:
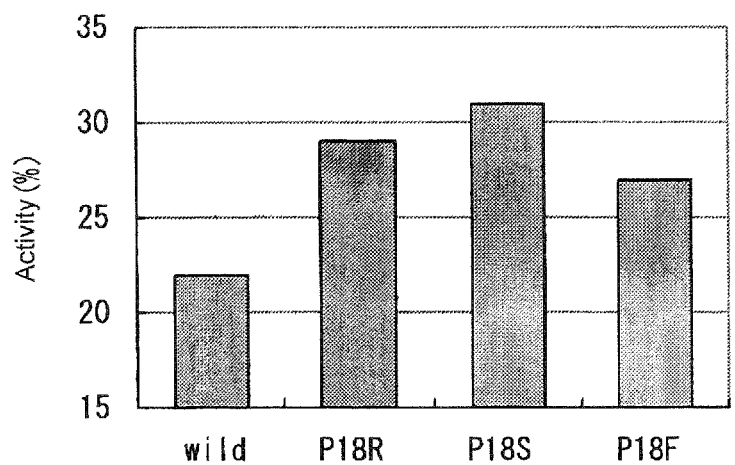
FIG. 19 is a graph showing comparison between a wild-type RNOK203 and its modified antibodies at position 18 in L chain for their heat stability when treated at 45° C. in ELISA.

As a result, it was found that P18R, P18S and P18F modified RNOK203 antibodies exhibited increased heat stability (FIG. 19).

Example 33: Assessment of Tolerance Against Acid of Modified Antibodies at Position 18 in L Chain with RNOK203

Figure 20:
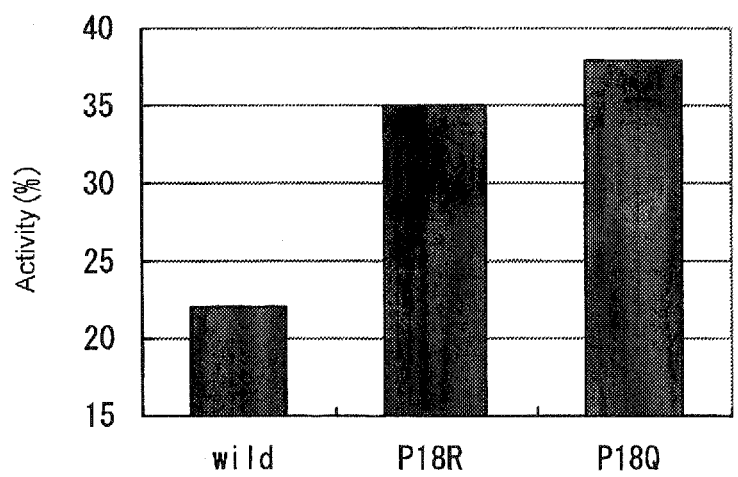
FIG. 20 is a graph showing comparison between a wild-type RNOK203 and its modified antibodies at position 18 in L chain for their tolerance against an acid when treated at pH 4.0 in ELISA.

The culture supernatant fractions of wild-type RNOK203/ its modified antibodies were diluted to 50 μL/tube with Block Ace and adjusted to pH 4.0 with 1N HCl and a pH meter (HORIBA) and treated at 25° C. for 2 hours. The samples were then adjusted to pH 7 with 1M Tris-HCl (pH 9.5) and subjected to ELISA where a ratio of the obtained absorbance to that of untreated samples was shown as a residual activity in a graph for comparison between the modified antibodies. As a result, it was found that P18F, P18A, P18W, P18L, P18%, P18Q and P18S modified RNOK203 antibodies exhibited increased tolerance against an acid. Typical results are shown in a graph (FIG. 20) whereas the results of the remaining modified antibodies are summarized in Table 2 for a ratio of the respective residual activity to that of the wild-type antibody.

TABLE 2

| Modified antibodies | Comparison with wild-type (%) |
|---|---|
| P18F | 180 |
| P18A | 160 |
| P18W | 200 |
| P18L | 150 |
| P18R | 160 |
| P18Q | 170 |
| P18S | 140 |

Example 34: Assessment of Tolerance Against Freeze-Thawing of Modified Antibodies at Position 18 in L Chain with RNOK203

Figure 21:
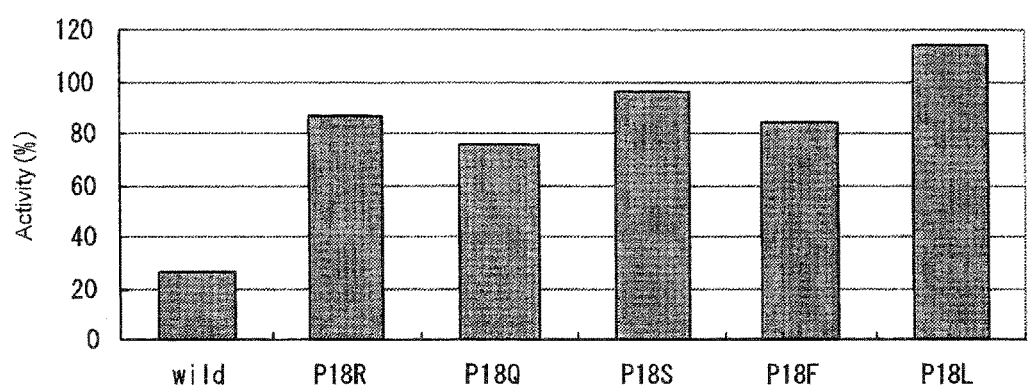
FIG. 21 is a graph showing comparison between a wild-type RNOK203 and its modified antibodies at position 18 in L chain for their tolerance against freeze-thawing in ELISA.

The culture supernatant fractions of wild-type RNOK203/ its modified antibodies were subjected to freeze-thawing repeated for either six times or only once and then to ELISA where a ratio of the absorbance obtained from the samples subjected to six freeze-thawing procedures to that of samples subjected to only one freeze-thawing procedure as a residual activity. As a result, it was found that P18R, P18Q, P18S, P18F and P18L modified RNOK203 antibodies exhibited increased tolerance against freeze-thawing (FIG. 21).

INDUSTRIAL APPLICABILITY

The method for improving the properties of a human antibody or a humanized antibody according to the present invention is characterized by that at least any one of the amino acid residues at position 8, 12, 15 or 18 (according to Kabat numbering) in a light chain variable region (hereinafter referred to as "VL chain") is substituted with a different amino acid other than proline or cysteine. With substitution of merely a single amino acid residue at such a specific position in an antibody, it is possible to obtain an antibody with an improved expression level and/or stability. Accordingly, a human antibody or a humanized antibody with an improved expression level and/or stability obtained by the method according to the present invention, as possessing all the features of high antigen specificity, low immunogenicity, high productivity and improved stability, may be extremely useful in the clinical field such as human diagnosis and therapy as a specific antibody targeting a disease-related antigen.

The invention claimed is:

1. A method for improving the expression level, stability, and/or acid tolerance of a human antibody or a humanized antibody, said method comprising:
   modifying a human antibody or a humanized antibody by substituting the amino acid at position 15 (according to Kabat numbering) in a light chain variable region (hereinafter referred to as "VL chain") of the human antibody or the humanized antibody with a different amino acid other than proline or cysteine and selected from any one of the amino acid substitutions as described in (1) to (3) below:
   (1) to improve the expression level of the antibody; substitution of Pro with Arg, Ser or Gly, or substitution of Leu with Arg,
   (2) to improve the heat stability of the antibody; substitution of Pro with Arg, Ser, Gly or Phe, or substitution of Val with Arg or Ser, and
   (3) to improve the acid tolerance of the antibody; substitution of Pro with Arg, Ser, Gly or Phe, or substitution of Leu with Arg, or substitution of Val with Arg or Ser, wherein said VL chain belongs to any one of the human Vκ1 family, the human Vκ2 family or the human Vκ3 family, and having a framework (FR) 1, which prior to substitution, has the FR1 sequence encoded by SEQ ID NO:31 from DPK9, encoded by SEQ ID NO:32 from DPK18, or encoded by SEQ ID NO:33 from DPK22, respectively, to thereby obtain a modified human antibody or a modified humanized antibody having improved expression level, stability and/or acid tolerance as compared to a control, which is identical to the human antibody or the humanized antibody but without said substitution.

2. The method according to claim 1, wherein the amino acid residue at position 15 after substitution in the VL chain belonging to human Vκ1 family is Arg or Ser.

3. The method according to claim 2, wherein FR1 of said VL chain belonging to human Vκ1 family prior to substitution has the sequence from DPK9 (GeneBank Accession No. X59315).

4. The method according to claim 2, wherein FR1 of the VL chain belonging to human Vκ1 family after substitution has the amino acid sequence selected from the amino acid sequences as depicted in SEQ ID NO: 2 to 7.

5. The method according to claim 1, wherein the amino acid residue at position 15 after substitution in the VL chain belonging to human Vκ2 family is Arg.

6. The method according to claim 5, wherein FR1 of said VL chain belonging to human Vκ2 family prior to substitution has the sequence from DPK18 (GeneBank Accession No. X63403).

7. The method according to claim 5, wherein FR1 of the VL chain belonging to human Vκ2 family after substitution has the amino acid sequence selected from the amino acid sequences as depicted in SEQ ID NO: 9 to 25.

8. The method according to claim 1, wherein said substitution occurs in the VL chain belonging to the human Vκ3 family and results in an Arg, Ser, Gly, or Phe residue at position 15.

9. The method according to claim 8, wherein framework (FR) 1 of said VL chain belonging to the human Vκ3 family prior to substitution has the FR1 sequence encoded by SEQ ID NO:33 from DPK22.

10. The method according to claim 8, wherein framework (FR) 1 of the VL chain belonging to the human Vκ3 family after substitution has the amino acid sequence selected from the group consisting of SEQ ID NO: 27 to 30.

11. The method according to claim 1, wherein said antibody is an intact antibody, or an antibody fragment such as Fab, Fab', F(ab')$_2$, scAb, scFv, diabody [a recombinant dimer antibody consisting of homologous or heterologous heavy chain variable region (VH chain) and VL chain connected by a short linker peptide] or scFv-Fc; or a fused antibody or a fused antibody fragment with other proteins; or an antibody or an antibody fragment labeled with a low molecular weight compound; or an antibody or an antibody fragment modified with a high molecular weight compound.

12. The method according to claim 1, wherein the amino acid substitution is done by a genetic recombination technique.

13. The method according to claim 1, wherein framework (FR) 1 of the VL chain belonging to the human Vκ1, Vκ2 or Vκ3 family after substitution has the amino acid sequence selected from the group consisting of SEQ ID NO: 2 to 7, the group consisting of SEQ ID NO: 9 to 25, or the group consisting of SEQ ID NO: 27 to 30, respectively.

* * * * *

SEQUENCE LISTING

```
<160> NUMBER OF SEQ ID NOS: 33

<210> SEQ ID NO 1
<211> LENGTH: 23
<212> TYPE: PRT
<213> ORGANISM: Homo sapiens

<400> SEQUENCE: 1

Asp Ile Val Met Thr Gln Ser Pro Ser Ser Leu Ser Ala Ser Val Gly
1               5                   10                  15

Asp Thr Val Thr Ile Thr Cys
            20

<210> SEQ ID NO 2
<211> LENGTH: 23
<212> TYPE: PRT
<213> ORGANISM: Homo sapiens

<400> SEQUENCE: 2

Asp Ile Val Met Thr Gln Ser Gly Ser Ser Leu Ser Ala Ser Val Gly
1               5                   10                  15

Asp Thr Val Thr Ile Thr Cys
            20

<210> SEQ ID NO 3
<211> LENGTH: 23
<212> TYPE: PRT
```

<213> ORGANISM: Homo sapiens

<400> SEQUENCE: 3

Asp Ile Val Met Thr Gln Ser Thr Ser Ser Leu Ser Ala Ser Val Gly
1               5                   10                  15

Asp Thr Val Thr Ile Thr Cys
            20

<210> SEQ ID NO 4
<211> LENGTH: 23
<212> TYPE: PRT
<213> ORGANISM: Homo sapiens

<400> SEQUENCE: 4

Asp Ile Val Met Thr Gln Ser Arg Ser Ser Leu Ser Ala Ser Val Gly
1               5                   10                  15

Asp Thr Val Thr Ile Thr Cys
            20

<210> SEQ ID NO 5
<211> LENGTH: 23
<212> TYPE: PRT
<213> ORGANISM: Homo sapiens

<400> SEQUENCE: 5

Asp Ile Val Met Thr Gln Ser Ser Ser Ser Leu Ser Ala Ser Val Gly
1               5                   10                  15

Asp Thr Val Thr Ile Thr Cys
            20

<210> SEQ ID NO 6
<211> LENGTH: 23
<212> TYPE: PRT
<213> ORGANISM: Homo sapiens

<400> SEQUENCE: 6

Asp Ile Val Met Thr Gln Ser Pro Ser Ser Leu Ser Ala Ser Arg Gly
1               5                   10                  15

Asp Thr Val Thr Ile Thr Cys
            20

<210> SEQ ID NO 7
<211> LENGTH: 23
<212> TYPE: PRT
<213> ORGANISM: Homo sapiens

<400> SEQUENCE: 7

Asp Ile Val Met Thr Gln Ser Pro Ser Ser Leu Ser Ala Ser Ser Gly
1               5                   10                  15

Asp Thr Val Thr Ile Thr Cys
            20

<210> SEQ ID NO 8
<211> LENGTH: 23
<212> TYPE: PRT
<213> ORGANISM: Homo sapiens

<400> SEQUENCE: 8

Asp Val Val Met Thr Gln Thr Pro Leu Ser Leu Pro Val Thr Leu Gly
1               5                   10                  15

Gln Pro Ala Ser Ile Ser Cys
            20

<210> SEQ ID NO 9
<211> LENGTH: 23
<212> TYPE: PRT
<213> ORGANISM: Homo sapiens

<400> SEQUENCE: 9

Asp Val Val Met Thr Gln Thr Pro Leu Ser Leu Ser Val Thr Leu Gly
1               5                   10                  15

Gln Pro Ala Ser Ile Ser Cys
            20

<210> SEQ ID NO 10
<211> LENGTH: 23
<212> TYPE: PRT
<213> ORGANISM: Homo sapiens

<400> SEQUENCE: 10

Asp Val Val Met Thr Gln Thr Pro Leu Ser Leu His Val Thr Leu Gly
1               5                   10                  15

Gln Pro Ala Ser Ile Ser Cys
            20

<210> SEQ ID NO 11
<211> LENGTH: 23
<212> TYPE: PRT
<213> ORGANISM: Homo sapiens

<400> SEQUENCE: 11

Asp Val Val Met Thr Gln Thr Pro Leu Ser Leu Val Val Thr Leu Gly
1               5                   10                  15

Gln Pro Ala Ser Ile Ser Cys
            20

<210> SEQ ID NO 12
<211> LENGTH: 23
<212> TYPE: PRT
<213> ORGANISM: Homo sapiens

<400> SEQUENCE: 12

Asp Val Val Met Thr Gln Thr Pro Leu Ser Leu Gly Val Thr Leu Gly
1               5                   10                  15

Gln Pro Ala Ser Ile Ser Cys
            20

<210> SEQ ID NO 13
<211> LENGTH: 23
<212> TYPE: PRT
<213> ORGANISM: Homo sapiens

<400> SEQUENCE: 13

Asp Val Val Met Thr Gln Thr Pro Leu Ser Leu Leu Val Thr Leu Gly
1               5                   10                  15

Gln Pro Ala Ser Ile Ser Cys
            20

<210> SEQ ID NO 14
<211> LENGTH: 23
<212> TYPE: PRT
<213> ORGANISM: Homo sapiens

<400> SEQUENCE: 14

-continued

Asp Val Val Met Thr Gln Thr Pro Leu Ser Leu Arg Val Thr Leu Gly
1               5                   10                  15

Gln Pro Ala Ser Ile Ser Cys
            20

<210> SEQ ID NO 15
<211> LENGTH: 23
<212> TYPE: PRT
<213> ORGANISM: Homo sapiens

<400> SEQUENCE: 15

Asp Val Val Met Thr Gln Thr Pro Leu Ser Leu Phe Val Thr Leu Gly
1               5                   10                  15

Gln Pro Ala Ser Ile Ser Cys
            20

<210> SEQ ID NO 16
<211> LENGTH: 23
<212> TYPE: PRT
<213> ORGANISM: Homo sapiens

<400> SEQUENCE: 16

Asp Val Val Met Thr Gln Thr Pro Leu Ser Leu Met Val Thr Leu Gly
1               5                   10                  15

Gln Pro Ala Ser Ile Ser Cys
            20

<210> SEQ ID NO 17
<211> LENGTH: 23
<212> TYPE: PRT
<213> ORGANISM: Homo sapiens

<400> SEQUENCE: 17

Asp Val Val Met Thr Gln Thr Pro Leu Ser Leu Glu Val Thr Leu Gly
1               5                   10                  15

Gln Pro Ala Ser Ile Ser Cys
            20

<210> SEQ ID NO 18
<211> LENGTH: 23
<212> TYPE: PRT
<213> ORGANISM: Homo sapiens

<400> SEQUENCE: 18

Asp Val Val Met Thr Gln Thr Pro Leu Ser Leu Pro Val Thr Arg Gly
1               5                   10                  15

Gln Pro Ala Ser Ile Ser Cys
            20

<210> SEQ ID NO 19
<211> LENGTH: 23
<212> TYPE: PRT
<213> ORGANISM: Homo sapiens

<400> SEQUENCE: 19

Asp Val Val Met Thr Gln Thr Pro Leu Ser Leu Pro Val Thr Leu Gly
1               5                   10                  15

Gln Arg Ala Ser Ile Ser Cys
            20

<210> SEQ ID NO 20
<211> LENGTH: 23

```
<212> TYPE: PRT
<213> ORGANISM: Homo sapiens

<400> SEQUENCE: 20

Asp Val Val Met Thr Gln Thr Pro Leu Ser Leu Pro Val Thr Leu Gly
 1               5                  10                  15

Gln Ser Ala Ser Ile Ser Cys
            20

<210> SEQ ID NO 21
<211> LENGTH: 23
<212> TYPE: PRT
<213> ORGANISM: Homo sapiens

<400> SEQUENCE: 21

Asp Val Val Met Thr Gln Thr Pro Leu Ser Leu Pro Val Thr Leu Gly
 1               5                  10                  15

Gln Phe Ala Ser Ile Ser Cys
            20

<210> SEQ ID NO 22
<211> LENGTH: 23
<212> TYPE: PRT
<213> ORGANISM: Homo sapiens

<400> SEQUENCE: 22

Asp Val Val Met Thr Gln Thr Pro Leu Ser Leu Pro Val Thr Leu Gly
 1               5                  10                  15

Gln Ala Ala Ser Ile Ser Cys
            20

<210> SEQ ID NO 23
<211> LENGTH: 23
<212> TYPE: PRT
<213> ORGANISM: Homo sapiens

<400> SEQUENCE: 23

Asp Val Val Met Thr Gln Thr Pro Leu Ser Leu Pro Val Thr Leu Gly
 1               5                  10                  15

Gln Trp Ala Ser Ile Ser Cys
            20

<210> SEQ ID NO 24
<211> LENGTH: 23
<212> TYPE: PRT
<213> ORGANISM: Homo sapiens

<400> SEQUENCE: 24

Asp Val Val Met Thr Gln Thr Pro Leu Ser Leu Pro Val Thr Leu Gly
 1               5                  10                  15

Gln Leu Ala Ser Ile Ser Cys
            20

<210> SEQ ID NO 25
<211> LENGTH: 23
<212> TYPE: PRT
<213> ORGANISM: Homo sapiens

<400> SEQUENCE: 25

Asp Val Val Met Thr Gln Thr Pro Leu Ser Leu Pro Val Thr Leu Gly
 1               5                  10                  15

Gln Gln Ala Ser Ile Ser Cys
```

```
               20

<210> SEQ ID NO 26
<211> LENGTH: 23
<212> TYPE: PRT
<213> ORGANISM: Homo sapiens

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 27
<211> LENGTH: 23
<212> TYPE: PRT
<213> ORGANISM: Homo sapiens

<400> SEQUENCE: 27

Glu Ile Val Leu Thr Gln Ser Pro Gly Thr Leu Ser Leu Ser Arg Gly
1               5                   10                  15

Glu Arg Ala Thr Leu Ser Cys
            20

<210> SEQ ID NO 28
<211> LENGTH: 23
<212> TYPE: PRT
<213> ORGANISM: Homo sapiens

<400> SEQUENCE: 28

Glu Ile Val Leu Thr Gln Ser Pro Gly Thr Leu Ser Leu Ser Ser Gly
1               5                   10                  15

Glu Arg Ala Thr Leu Ser Cys
            20

<210> SEQ ID NO 29
<211> LENGTH: 23
<212> TYPE: PRT
<213> ORGANISM: Homo sapiens

<400> SEQUENCE: 29

Glu Ile Val Leu Thr Gln Ser Pro Gly Thr Leu Ser Leu Ser Gly Gly
1               5                   10                  15

Glu Arg Ala Thr Leu Ser Cys
            20

<210> SEQ ID NO 30
<211> LENGTH: 23
<212> TYPE: PRT
<213> ORGANISM: Homo sapiens

<400> SEQUENCE: 30

Glu Ile Val Leu Thr Gln Ser Pro Gly Thr Leu Ser Leu Ser Phe Gly
1               5                   10                  15

Glu Arg Ala Thr Leu Ser Cys
            20

<210> SEQ ID NO 31
<211> LENGTH: 1009
<212> TYPE: DNA
<213> ORGANISM: Homo sapiens

<400> SEQUENCE: 31
```

```
ctgcagctgt gctcagcctg ccccatgccc tgctgattga tttgcatgtt ccagagcaca      60 gcccctgcc ctgaagactt ttttatgggc tggtcgcacc ctgtgcagga gtcagtctca      120
gtcaggacac agcatggaca tgagggtccc cgctcagctc ctgggctcc tgctactctg      180 gctccgaggt aaggatggag aacactagga atttactcag ccagtgtgct cagtactgac      240
tggaacttca gggaagttct ctgataacat gattaatagt aagaatattt gttttttatgt   300 ttccaatctc aggtgccaga tgtgacatcc agatgaccca gtctccatcc tccctgtctg    360
catctgtagg agacagagtc accatcactt gccgggcaag tcagagcatt agcagctatt    420
taaattggta tcagcagaaa ccagggaaag cccctaagct cctgatctat gctgcatcca   480
gtttgcaaag tggggtccca tcaaggttca gtggcagtgg atctgggaca gatttcactc    540
tcaccatcag cagtctgcaa cctgaagatt ttgcaactta ctactgtcaa cagagttaca    600
gtacccctcc cacagtgtta caagtcataa cataaacctc caaggaagca gatgtgtgag    660
gacgagccac cccagatgct cctcctggtg cctccatctg ctgagagcat ttctcaaact    720
cagtcaggtt ttgaaagtca ttgggagact tttgtagagg ggaccaggga ggctcctctg    780
aactctaagc ctcttttgcc cctatcccca ggagaaaaga tgtgacaatg cctgtcctga    840
ttgaataagg aagagataca agtccacctg aggagtctgt gttatgggat aattggaatt    900
tacacagcaa aagagaagct attctcggta tttcaaggag aaattgttca agttgaataa    960
attagagtct aaactagtct ttttgaagct acggtatgtt attcgtgaa               1009

<210> SEQ ID NO 32
<211> LENGTH: 1883
<212> TYPE: DNA
<213> ORGANISM: Homo sapiens

<400> SEQUENCE: 32
ggattcaatt atccagtgaa agtatgcatt caaataaaa gtaaagtaaa aacatttctt      60
gataaacaaa aatgaagaga ataaattact taaagacatg ctgtataaca atttatctag   120
gaaattcttc agattcacaa aaaatgacag cagacagtaa cttgaatctg taaggaggaa   180
ggaaggcctc aaaagtacta agggaacaaa aaaagagcta gaccaaacca acatgtttac    240
ttccgtttat atgaggtttc gtatagggaa agccaatcta tttggacaga tgtcagaatg    300 ccagttttcct tgattgggat gggaaacagc tgtttcctga aggtaggta catgagggaa    360 gaatctggag attctgcagt attctacagt ttaatctcgg tggagaatat atgtaaaact    420
ttattcggtt gcactttta acatttctgt cttttactt tgtgtgtttt tatttaaatt      480
tttaaaaaat tgaaagggcc aaatctgaac tctttttaaac aaaaatgaac aaaaacataa    540
gaattagtaa atatttgtgg aaacatggcc ttattaacaa gaagtataaa atgtgcctgg    600
gagagtacta tgaaacaaga aatctgttag ggaagacaga aggaaatact taaatttctc    660
caacatagac agcatagatt ttatgcctat tcgtttccct ccaaacagag aagatattta    720
agtcattttg ctcacaagag aggctcctac cctccccttg gctctttcca ccccactgca    780
cccaccaggt gatttgcata ttatcccctta gtgaagactt tccttgtgag tctgagataa    840
aagctcagct ctaccccttgc cttgactgat caggactcct cagttcacct tctcacaatg    900
aggctccctg ctcagctcct ggggctgcta atgctctggg tcccaggtaa gggtagaagg    960
gagatgaggg aggagaatgg catggaacgg tgagttctgg ggccccactg cctctaacaa    1020
cagtgatctc tgggggtctc actacactcc tatgtgtgtt cctttcctgt attggacatg    1080
```

```
cacatgttgt cctccagagt ggggcatgtg atgatcagat ctgtgagagt gaggaagatt    1140
caagcagaaa caaggatctg tgctctgggg aagactgaca cagaaagggg atggtgtggg    1200
gtcttctgga gaccccttttg agccttggat cccttgagtt ccattttgaa actgtgtatt    1260
tttgaaatat gaacaaatac atatatagcc tgaaataaac aacaaatcaa aatttatgaa    1320
aattacacat aaactttata cataaccttg ctcttctttc tatttatttc aggatccagt    1380
ggggatgttg tgatgactca gtctccactc tccctgcccg tcacccttgg acagccggcc    1440
tccatctcct gcaggtctag tcaaagcctc gtatacagtg atggaaacac ctacttgaat    1500
tggtttcagc agaggccagg ccaatctcca aggcgcctaa tttataaggt ttctaaccgg    1560
gactctgggg tcccagacag attcagcggc agtgggtcag gcactgattt cacactgaaa    1620
atcagcaggg tggaggctga ggatgttggg gtttattact gcatgcaagg tacacactgg    1680
cctcccacag tggtacagcc ctgaacaaaa acctccctgt ggagtggccc agctgcccac    1740
atgtggtgct tgtctgggga gcagctcagc agggtctcag aatctgtgta agaggaagat    1800
gctggagaac cagggaacaa ttcacatctg aggactctgg actttgagag cccagccaca    1860
actcaggcac cacatccttt atg                                            1883

<210> SEQ ID NO 33
<211> LENGTH: 290
<212> TYPE: DNA
<213> ORGANISM: Homo sapiens

<400> SEQUENCE: 33
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctcc                290
```